US009358310B2

(12) United States Patent
Katti et al.

(10) Patent No.: US 9,358,310 B2
(45) Date of Patent: Jun. 7, 2016

(54) EGCG STABILIZED GOLD NANOPARTICLES AND METHOD FOR MAKING SAME

(71) Applicant: The Curators of the University of Missouri, Columbia, MO (US)

(72) Inventors: Kattesh V. Katti, Columbia, MO (US); Raghuraman Kannan, Columbia, MO (US); Kativa K. Katti, Columbia, MO (US); Satish Kumar Nune, Lawrence, KS (US); Cathy S. Cutler, Columbia, MO (US); Charles Caldwell, Columbia, MO (US); Ravi Shukla, Columbia, MO (US); Nripen Chanda, Columbia, MO (US); Ajit Zambre, Columbia, MO (US); Anandhi Upendran, Columbia, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

(21) Appl. No.: 13/668,916

(22) Filed: Nov. 5, 2012

(65) Prior Publication Data
US 2013/0129618 A1    May 23, 2013

Related U.S. Application Data

(63) Continuation-in-part of application No. 12/283,935, filed on Sep. 17, 2008, now Pat. No. 8,333,994.

(60) Provisional application No. 61/628,717, filed on Nov. 4, 2011, provisional application No. 60/994,111, filed on Sep. 17, 2007.

(51) Int. Cl.
| | |
|---|---|
| A61K 9/14 | (2006.01) |
| A61K 9/16 | (2006.01) |
| A61K 51/00 | (2006.01) |
| A61K 51/12 | (2006.01) |
| A61K 33/24 | (2006.01) |
| A61K 41/00 | (2006.01) |

(52) U.S. Cl.
CPC ............ *A61K 51/1251* (2013.01); *A61K 9/148* (2013.01); *A61K 33/24* (2013.01); *A61K 41/00* (2013.01)

(58) Field of Classification Search
None
See application file for complete search history.

(56) References Cited

U.S. PATENT DOCUMENTS

| 5,541,289 | A | 7/1996 | Gilbertson |
| 6,103,868 | A | 8/2000 | Heath et al. |
| 6,572,673 | B2 | 6/2003 | Lee et al. |
| 6,818,199 | B1 | 11/2004 | Hainfeld et al. |
| 2005/0009170 | A1 | 1/2005 | Gardea-Torresdey et al. |
| 2005/0054613 | A1 | 3/2005 | Katti et al. |
| 2006/0127505 | A1 | 6/2006 | Haines et al. |
| 2007/0051202 | A1 | 3/2007 | Raghuraman et al. |
| 2007/0299133 | A1 | 12/2007 | Mehansho et al. |
| 2008/0076119 | A9 | 3/2008 | Sun et al. |
| 2009/0074674 | A1 | 3/2009 | Katti et al. |
| 2009/0232853 | A1 | 9/2009 | Harris |

FOREIGN PATENT DOCUMENTS

| WO | WO 03/072053 | 9/2003 |
| WO | WO 2007/027978 | 3/2007 |
| WO | WO 2009/005752 | 1/2009 |
| WO | WO 2010/139942 | 12/2010 |

OTHER PUBLICATIONS

Yoosaf, K., et al., "In Situ Synthesis of Metal Nanoparticles and Selective Naked-Eye Detection of Lead Ions from Aqueous Media", 2007, J Phys. Chem. C, pp. 12839-12847.*
Jovanovic, S,V., et al. "Antioxidant Potential of Gallocatechins. A Pulse Radiolysis and Laser Photolysis Study", 1995, JACS, pp. 9881-9888.*
Kannan, R., et al., "Nanocompatible Chemistry toward Fabrication of Target-Specific Gold Nanoparticles", 2006, JACS, pp. 11342-11343.*
Tsuji, M., et al., "Synthesis of gold nanorods and nanowires by a microwave—polyol method", 2004, Materials Letters, pp. 2326-2330.*
Sah, J.F., et al. "Epigallocatechin-3-gallate Inhibits Epidermal Growth Factor Receptor Signaling Pathway", 2004, JBC, pp. 12755-12762.*
Vickers, M.S., et al., "Dithiocarbamate ligand stabilised gold nanoparticles", 2006, J. Mater. Chem., pp. 209-215.*
Balogh, Lajos P., et. al., "Development of dendrimer-gold radioactive nanocomposites to treat cancer microvasculature," *Biotechnology*, vol. 2, No. 4, 2003, pp. 94-44.
Bhattacharya, Santanu, et. al. "Synthesis of gold nanoparticles stabilised by metal-chelator and the controlled formation of close-packed aggregates by them," Proc. Indian Acad. Sci. (Chem. Sci), vol. 115, Nos. 5 & 6, Oct.-Dec. 2003, pp. 613-619.
(Continued)

*Primary Examiner* — Michael G Hartley
*Assistant Examiner* — Lance Rider
(74) *Attorney, Agent, or Firm* — Greer, Burns & Crain, Ltd.

(57) ABSTRACT

The invention provides stabilized, biocompatible gold nanoparticles that are stabilized with material from epigallocatechin Gallate (EGCg), which is a polyphenols- or flavonoids-rich plant material that can be obtained from green tea. The EGCg is an antioxidant reducing agent derived from green tea. The gold nanoparticles of the invention can be radioactive or non radioactive and are formed via a simple room temperature fabrication method. In preferred embodiment method of making, an aqueous solution containing gold salts is provided. The aqueous solution is mixed with EGCg in a buffer, such as deionized water. The gold salts react to form biocompatible gold nanoparticles that are stabilized with a coating of EGCg. The thermodynamically feasible redox couple of AuCl4-/EGCg leading to the reduction of AuCl4- by EGCg to form gold nanoparticles. In another embodiment, pre-cooled gold salt and EGCg solutions form multi-layered EGCg coated particles.

17 Claims, 10 Drawing Sheets

(56) References Cited

OTHER PUBLICATIONS

Brust M., et. al., "Synthesis of Thiol-Derivatised Gold Nanoparticles in a Two-Phase Liquid-Liquid System", *Journal of the Chemical Society-Chemical Communications*, vol. 7, 1994, pp. 801-802.
Chen J., et. al. "Gold Nanocages: Bioconjugation and Their Potential Use as Optical Imaging Contrast Agents", *Nano Letters*, vol. 5, No. 3, 2005; pp. 473-477.
Gardea-Torresdey, Jorge, "Plants with Midas Touch: Formation of Gold Nanoparticles by Alfalfa Plants," Believed published circa 2002 on the World Wide Web at: http://www-ssrl.slac.stanford.edu/research/highlights_archive/alfalfa.html.
Gierada, D. S.; et. al., "Gadolinium as a CT contrast agent: Assessment in a porcine model", *Radiology*, vol. 210, 1999, pp. 829-834.
Hainfeld, J. F.; et. al., "Gold nanoparticles: a new X-ray contrast agent", *British Journal of Radiology*, vol. 79, 2006, pp. 248-253.
He, S., et. al., "Superlattices of Silver Nanoparticles Passivated by Mercaptan," *Journal of Physics D: Applied Physics*, vol. 34, 2001, pp. 3425-3429.
Kalaugher, L., "Green Technique Makes Silver Nanoparticles,", www.nanotechweb.org/articles/news/3/1/1/1, Jan. 2004.
Kannan R, et. al.., "Nanocompatible chemistry toward fabrication of target-specific gold nanoparticles", *Journal of the American Chemical Society*, vol. 128, No. 35, 2006; pp. 11342-11343.
Katti, Kattumuri, V. et. al., "Gum arabic as a phytochemical construct for the stabilization of gold nanoparticles: In vivo pharmacokinetics and X-ray-contrast-imaging studies", *Small*, vol. 3, No. 2, 2007, pp. 333-341.
Katti, Kattumuri V, et. al.., "Agarose-stabilized gold nanoparticles for surface-enhanced Raman spectroscopic detection of DNA nucleosides", *Applied Physics Letters*, vol. 88, No. 15, 2006, pp. 153114-1-153114-3.
Kim, Beomseok, et. al., "Tuning the Optical Properties of Large Gold Nanoparticle Arrays," *Mat. Res. Soc. Symp. Proc.*, vol. 676, 2001.
Kim, Beomseok, et. al., "Self-Organization of Large Gold Nanoparticle Arrays," *J. Am. Chem. Soc.*, vol. 123, 2001, pp. 7955-7956.
Pastoriza-Santos, I., et al., "Reduction of Silver Nanoparticles in DMF. Formation of Monolayers and Stable Colloids,", *Pure Appl. Chem.*, vol. 72, Nos. 1-2, 2002, pp. 83-90.
Peters R., "Nanoscopic medicine: The next frontier", *Small* vol. 2, No. 4, 2006 pp. 452-456.
Kandikere Ramaiah Prabhu et al. "*De novo* synthetic design for air-stable *bis* primary phosphines: Synthetic, catalytic and biomedical motifs," Special Section: Non-Metal Chemistry; Current Science, vol. 78, No. 4, Feb. 25, 2000.
Rosset, A, et. al., "OsiriX: An open-source software for navigating in multidimensional DICOM images", *Journal of Digital Imaging*, vol. 17. No. 3, 2004, pp. 205-216.
Sokolov K, et. al., "Optical systems for In vivo molecular imaging of cancer", *Technology in Cancer Research & Treatment*, vol. 2, No. 5, 2003, pp. 487-594.
Spring, D. B., et. al., Dr Spring and colleagues respond: Safety of ionic and nonionic contrast media, *Radiology*, vol. 206, 1998, pp. 560-561.
Spring, D. B., et. al., "Nonfatal adverse reactions to iodinated contrast media: Spontaneous reporting to the U.S. Food and Drug Administration, 1978-1994", *Radiology*, vol. 204, 1997, pp. 325-332.
Spring, D. B., et. al., "Deaths related to iodinated contrast media reported spontaneously to the U.S. Food and Drug Administration, 1978-1994: Effect of the availability of low-osmolality contrast medial", *Radiology*, vol. 204, 1997, pp. 333-337.
Volkert, W.A., et. al., "Therapeutic Radiopharmaceuticals," *Chem. Rev.*, vol. 99, No. 9; pp. 2269-2292, 1999.
Wagner V, et. al., "The emerging nanomedicine landscape", *Nature Biotechnology*, vol. 24, No. 10, 2006; pp. 1211-1217.
Yin et. al., "Synthesis and Characterization of Stable Aqueous Dispersion of Silver Nanoparticles Through the Tollens Process," *J. Mater. Chem.*, vol. 12, 2002, pp. 522-527.
Raghuraman, Kannan et. al., "Characterization of Supramolecular $(H_2O)_{18}$ Water Morphology and Water-Methanol $(H_2O)_{15}(CH_3OH)_3$ Clusters in a Novel Prosperous Functionalized Trimeric Amino Acid Host,"., *J. Am. Chem. Soc.*, vol. 125, No. 23, 2003, pp. 6955-6961.
RadiologicalSocietyofNorthAmerica Computed Tomography (CT). http://www.radiologyinfo.org/en/info.cfm?pg=bodyct., Sep. 18, 2008.
ImaginisMedicalResource http://www.imaginis.com/ct-scan/, 2008.
MedCompare Contrast Agents. http://www.medcompare.com/matrix/165/Contrast-Agents.html., 2008.
Chanda, Nripen, et al., "Radioactive gold nanoparticles in cancer therapy: therapeutic efficacy studies of GA-$^{198}$AuNP nanoconstruct in prostate tumor-bearing mice", *Nanomedicine: Nanotechnology, Biology, and Medicine*, 6 (2010), pp. 201-209.
Shukla, Ravi, et al., "Laminin receptor specific therapeutic gold nanoparticles ($^{198}$AuNP-EGCg) show efficacy in treating prostate cancer", *PNAS*, vol. 109, No. 31, Jul. 31, 2012, pp. 12426-12431.

* cited by examiner

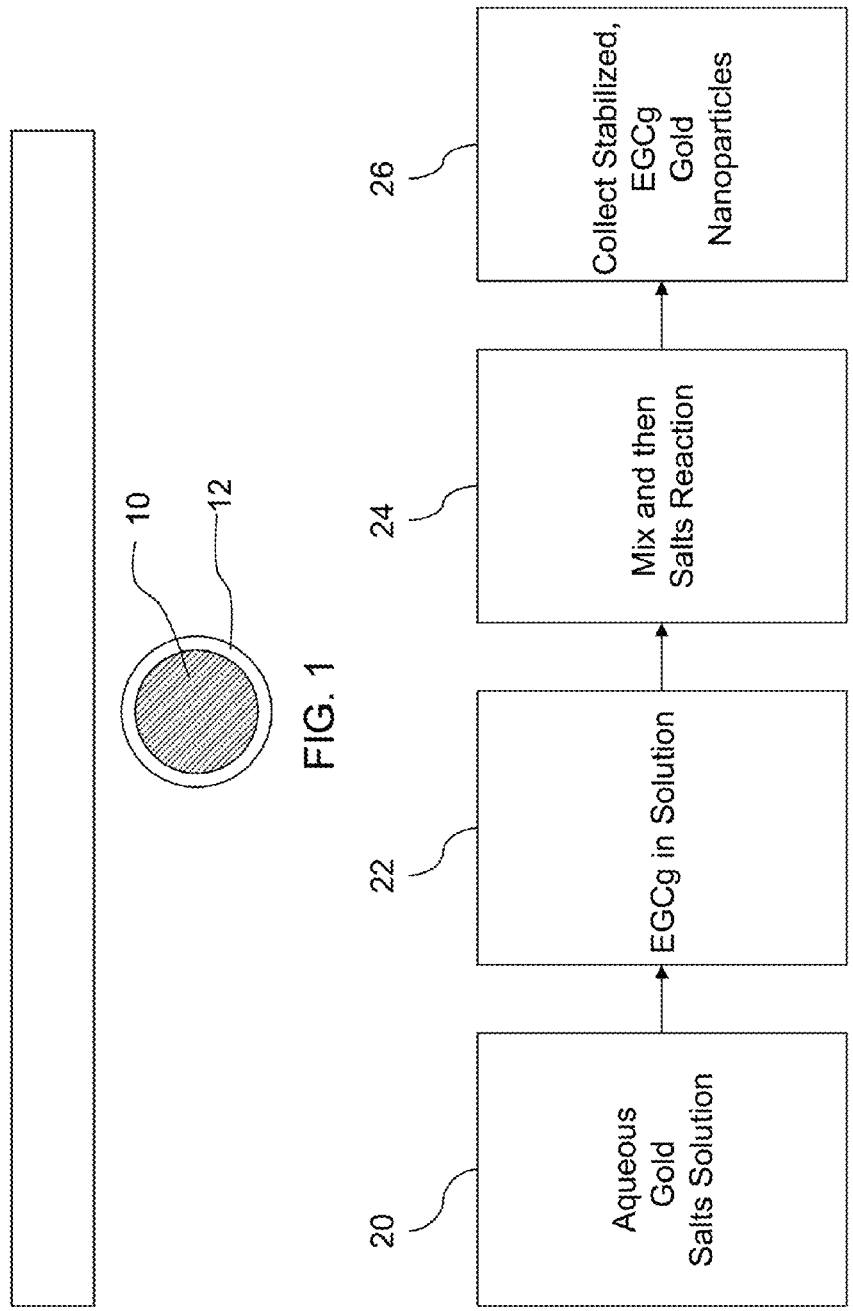

US 9,358,310 B2

EGCG STABILIZED GOLD NANOPARTICLES AND METHOD FOR MAKING SAME

PRIORITY CLAIM AND REFERENCE TO RELATED APPLICATION

This application claims priority under 35 U.S.C. §119 from prior provisional application Ser. No. 61/628,717, which was filed on Nov. 4, 2011. This application is a also continuation-in-part and claims priority under 35 U.S.C. §120 from prior co-pending application Ser. No. 12/283,935, now U.S. Pat. No. 8,333,994, which application claims priority under 35 U.S.C. §119 from prior provisional application Ser. No. 60/994,111, which was filed on Sep. 17, 2007.

STATEMENT OF GOVERNMENT INTEREST

This invention was made with government support under contract no. R01CA119412 awarded by the National Cancer Institute, and Grants No. 5R01CA119412 and 5R21CA128460 awarded by the National Institutes of Health. The government has certain rights in the invention.

FIELD

A field of the invention is gold nanoparticles. Example applications of the invention include medical diagnostics and medical therapies. Non-medical applications include sensors and electronic materials. Gold nanoparticles find use as therapeutic agents, sensors, electronic materials and coatings on biological and non-biological surfaces.

BACKGROUND

Nanomedicine is an emerging area of medicine that utilizes nanoparticles for the detection and treatment of various diseases and disorders. Nanoparticles are tiny fragments of) metals (or non metals) that are 100,000 times smaller than the width of human hair. Nanoparticles typically have different properties than naturally occurring bulk materials. Collateral properties emanate when materials, especially metals, are reduced to dimensions measured in nanometers. Nanoparticles exhibit properties that are unique from their corresponding naturally occurring bulk material.

Nanoparticles within the size range of about 1-50 nanometers have a size that can be correlated to cells, viruses, proteins and antibodies. The size resemblance that such nanoparticles have to living cells and cell components are of great interest to medical research because cells are primary components of all life (humans and animals).

Gold nanoparticles have a number of important potential medical applications. One application is hyperthermia treatment in which gold nanoparticles are heated with oscillating magnetic fields after being associated with a targeted cell, typically cancer cells. Other applications relate to biological imaging, as gold nanoparticles display photo absorbance or emission characteristics that can be used in imaging for the diagnosis of various diseases. Contrast enhancement is also provided by gold nanoparticles. For example, the selective absorption of X-rays by gold and other metallic nanoparticles provides measurable contrasts for use in computer tomographic (CT) imaging and other imaging techniques These and other important diagnostic and therapeutic properties are attainable only when metallic (or non metallic) materials are reduced to nanometer particle sizes.

Gold nanoparticles have unique properties that make them more attractive than other nanoparticles for many therapeutic, imaging, and sensing applications, and particularly in medical applications. Gold nanoparticles have an unoxidized state, whereas most of the surface of less noble metals get oxidized to a depth of several nanometers or more, often significantly reducing or obliterating the nanoscale properties of the nanoparticles. Gold nanoparticles are highly reactive, but biocompatible, making them especially well-suited for in viva imaging and therapy. Gold nanoparticles can also be coated with specific biomolecules including, monoclonal antibodies, aptamers, peptides and various receptor specific substrates. Receptor specific coated nanoparticles are used mainly for targeting three different markers that are over expressed on cancer cells. They include: matrix metalloproteases, epidermal growth actor receptor, and oncoproteins that are associated with human papillomavirus infection.

For such in vivo imaging and therapy applications, it is that gold nanoparticles be produced stabilized in a biologically benign medium. Many current methods of producing gold nanoparticles require the removal of unreacted chemicals and byproducts from the nanoparticles as the chemicals and byproducts are necessary to the synthesis of the gold nanoparticles. The chemicals and byproducts must be removed after the production of nanoparticles to make the nanoparticles biocompatible.

Typical known methods of making nanoparticles utilize harsh conditions, such as the application of sodium, borohydride to reduce $AuCl_4^-$. See, e.g., M. Brust et al, "Synthesis of Thiol-Derivatized Gold Nanoparticles in a 2-Phase Liquid-Liquid System" Journal of the Chemical Society-Chemical Communications (7):801-02 (1994). The method provides for the efficient production of gold nanoparticle, but is unsuitable in the presence of target specific peptides because sodium borohydride will reduce chemical functionalities present on peptide backbones, which can reduce or eliminate the biospecificity of biomolecules. The sodium borohydride reduction method also uses thiols to stabilize the gold nanoparticles from agglomeration. Thiol-gold nanoparticle interaction is strong and makes gold nanoparticles highly stable. Once the gold nanoparticles are stabilized by thiols, they cannot be readily transferred onto useful drug moieties including peptides, proteins and various biochemical vectors that are normally used to target diagnostic and therapeutic gold nanoparticles on to tumor and various disease sites in the body. Other methods that have been developed utilize chemical cocktails during nanoparticle production, and are not environmentally friendly in additional to having the drawbacks concerning stabilization, reactivity, and biocompatibility.

SUMMARY OF THE INVENTION

The invention provides stabilized, biocompatible gold nanoparticles that are stabilized with material from epigallocatechin Gallate (EGCg), which is a polyphenols- or flavonoids-rich plant material that can be obtained from green tea. The EGCg is an antioxidant reducing agent derived from green tea. The gold nanoparticles of the invention can be radioactive or non radioactive and are formed via a simple room temperature fabrication method. In preferred embodiment method of making, an aqueous solution containing gold salts is provided. The aqueous solution is mixed with EGCg in a buffer, such as deionized water. The gold salts react to form biocompatible gold nanoparticles that are stabilized with a coating of EGCg. The thermodynamically feasible redox couple of AuCl4-/EGCg leading to the reduction of AuCl4- by EGCg to form gold nanoparticles. In another embodiment, pre-cooled gold salt and EGCg solutions form multi-layered EGCg coated particles.

BRIEF DESCRIPTION OF THE DRAWINGS

FIG. 1 is a schematic diagram that illustrates a stabilized, biocompatible gold nanoparticle of the invention;

FIG. 2A illustrates a preferred method of fabricating a stabilized, biocompatible gold nanoparticle of the invention;

FIG. 10A illustrate EGCg-AuNP estimation via a present digestion method conducted with NaCN solution; FIG. 10B is a standard graph of increasing EGCg concentrations in 0.01M NaCN solution.

DETAILED DESCRIPTION OF THE PREFERRED EMBODIMENTS

Figure 2B:
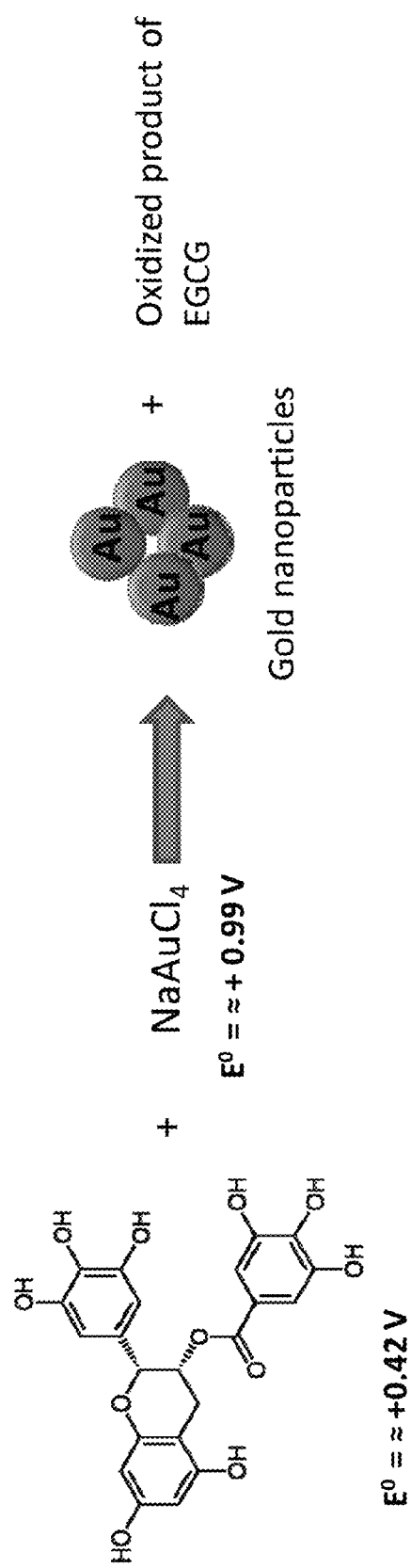
FIG. 2B illustrates the oxidation-reduction potential controls the direction of electron flow during gold nanoparticles synthesis.

The invention provides stabilized, biocompatible gold nanoparticles that are stabilized with material from polyphenols- or flavonoids-rich plant material, and specifically with EGCg obtained from green tea. The gold nanoparticles of the invention can be fabricated with an environmentally friendly method for making biocompatible stabilized gold nanoparticles.

In preferred embodiment methods of making, an aqueous solution containing radioactive or non-radioactive gold salts is provided. The aqueous solution is preferably provided in a solution that is made isotonic, such as via NaOH and buffered saline. The thermodynamically feasible redox couple of $AuCl_4^-$/EGCg leading to the reduction of $AuCl_4^-$ by EGCg to form gold nanoparticles.

Stabilized, biocompatible gold nanoparticles of the invention demonstrate an affinity for cancer cells and tissues. Accordingly, stabilized, biocompatible gold nanoparticles of the invention are well suited for diagnostic and therapeutic techniques that rely upon gold nanoparticles for imaging, contrast, or cell destruction. A preferred therapeutic is stabilized $^{198}$AuNP-EGCg. A method of sensing or therapy of the invention comprises introducing stabilized, biocompatible gold nanoparticles of the invention into a human or animal subject and conducting gold nanoparticle enhanced imaging or gold nanoparticle enhanced therapy. The radioactive gold nanoparticles ($^{198}$AuNP-EGCg) are inherently therapeutic, and are well-suited, for example, as therapeutic payloads in prostate tumors because of their (i) size; (ii) inherent affinity toward tumor vasculature and (iii) through their favorable radiochemical properties. Au-198 provides a desirable beta energy emission and half-life that destroys tumor cells/tumor tissue ($\beta_{max}$=0.96 MeV; half-life of 2.7 days). Its penetration range (up to 11 mm in tissue or up to 1100 cell diameters) is sufficiently long to provide cross-fire effects to destroy prostate tumor cells, but short enough to minimize radiation exposure to tissues near the capsule periphery.

Fabrication methods of the invention require only gold salts as precursors. No other man-made chemicals are employed in the overall fabrication process, and there are accordingly no harsh chemicals utilized in the fabrication or harsh byproducts formed during the fabrication. Fabrication processes of the invention are therefore environmentally friendly and biologically benign.

Gold nanoparticles produced by methods of the invention demonstrate a high affinity for cancer cells/tissue. Embodiments of the invention include the diagnostic and therapeutic use of gold nanoparticles produced by methods of the invention in molecular imaging and therapy of cancer and various diseases in animals and human subjects.

Preferred embodiments will now be discussed with respect to the drawings. The description includes descriptions of experiments. The drawings include schematic figures that are not to scale, which will be fully understood by skilled artisans with reference to the accompanying description. Features may be exaggerated for purposes of illustration. From the preferred embodiments and experiments, artisans will recognize additional features and broader aspects of the invention.

FIG. 1 is a schematic diagram that illustrates a stabilized, biocompatible gold nanoparticle of the invention. In FIG. 1, a gold nanoparticle 10 is coated with a layer EGCg material 12. In a preferred embodiment, the particle is $H^{198}Au$, which is well suited for cancer therapy, and especially well-suited for targeted prostate cancer therapy.

FIG. 2A illustrates a preferred method of fabricating a stabilized, biocompatible gold nanoparticle of the invention. In FIG. 2A, an aqueous solution containing gold salts is provided 20. In preferred embodiments, the solution is radioactive tetrachloroauric acid ($H^{198}AuCl_4$) was used in carrier $NaAuCl_4$ solution and adjusted to a neutral pH, e.g., pH 7, and made isotonic, such as by using NaOH and Delbecco's phosphate buffered saline. EGCg is provided in solution. The aqueous solution is mixed 24 with a solution of EGCg in deionized water. EGC is a naturally occurring polyphenols- or flavonoids-rich material that is obtained from green tea.

The gold salts are reacted at room temperature 24 to form biocompatible gold nanoparticles that are stabilized with a coating of the polyphenols EGCg plant material. The particles are collected 26, such as by filtering. The entire process can be conducted at room temperature in a reasonable period of a time. The entire process is conducted in the absence of any other reducing agent, and the EGCg is responsible for reduction. In another embodiment, multi-layer coated EGCg is formed via a process that uses pre-cooled gold salts. The pre-cooling is effective to produce a multi-layer EGCg coated radioactive or non-radioactive gold nanoparticles.

Preferred gold salts used in methods of the invention are either sodium tetrachloaurate or aurochloric acid. Gold nanoparticles produced by this process do not require any external chemical to stabilize the gold nanoparticles. While the invention is not limited to a particular mechanism and understanding of the reaction mechanism is not required to practice the described embodiments, it is believed that various phytochemicals present in EGCg are responsible for providing a robust coating on gold nanoparticles and thus, rendering stability against agglomerations.

The method of FIG. 2A produces gold nanoparticles that require no further purification, that are biocompatible and stable. While the particles are stable as produced, an additional stabilizing agent such as gum Arabic can provide additional stability.

No further treatment is required prior to use of the stabilized, biocompatible gold nanoparticles produced by the method in biomedical applications. The method produces stabilized, biocompatible gold nanoparticles that are suitable for use within the body (in vivo) for diagnostic imaging using X-ray contrast CT imaging for the detection of various diseases, disorders and cancer. The gold nanoparticles are also suitable as X-ray enhancers in X-ray therapy of diseases including cancer. The stabilized, biocompatible gold nanoparticles are also useful for localized heating of targeted cells, namely hyperthermia treatment. Stabilized, biocompatible gold nanoparticles of the invention are suitable for direct administration into the human body through oral or intravenous routes.

Stabilized, biocompatible non-radioactive gold nanoparticles of the invention are biologically benign and therefore are also useful as coatings on skin, hair, for direct injections into specific tissue, for ingestion, etc. Stabilized, biocompatible gold nanoparticles are immediately suitable after fabrication by the FIG. 2A method. The nanoparticles are immediately ready for use in clinical CT imaging, X-ray induced cancer therapy and other diagnosis and therapeutic procedures, including cancer detection and treatment in animals and human beings. The radioactive particles are especially useful in cancer therapy. Stabilized, biocompatible gold nanoparticles of the invention are opaque to X-rays and provide excellent contrast between healthy and diseased tissue when viewed through X-ray CT images. They can be used in X-ray CT imaging for molecular imaging of cancer and various other diseases. They can also be used for the selective absorption of high energy X-rays in cancer therapy. Stabilized, biocompatible gold nanoparticle particles of the invention possess inherent high affinity toward gastrin releasing peptide receptors present on various types of cancerous cells such as cancerous cells of the prostate and breast cancer cells.

FIG. 2B shows that the oxidation-reduction potential controls the direction of electron flow during gold nanoparticles synthesis. The redox potential of the $AuCl_4^-/Au$ is 0.99 V (SHE), significantly positive than Epigallocatechin Gallate (0.42 V) and therefore redox chemistry drives the nanoparticles synthesis.

Initial Experimental Results

Stabilized, biocompatible gold nanoparticles have been produced in experiments that are consistent with the FIG. 2 method of fabrication. The stabilized, biocompatible gold nanoparticles were tested and characterized. The experiments will now be described, and artisans will appreciate additional aspects of the invention from the experiments. Artisans will also recognize that the experiments do not limit the invention and that commercial scale fabrication processes consistent with the invention may use different equipment, batch sizes and specific procedures related to the equipment and batch sizes.

Figure 3:
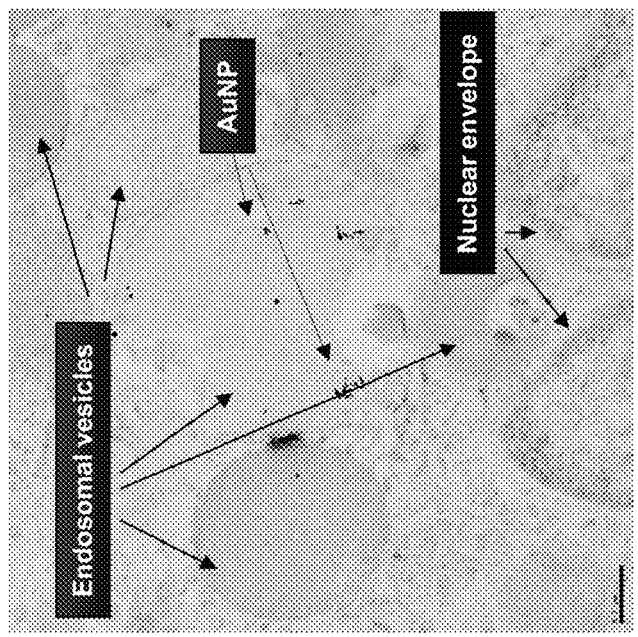
FIG. 3 is an image of a cell that has internalized stabilized, biocompatible gold nanoparticles of the invention.

On experiment was conducted to test stabilized, biocompatible gold nanoparticles of the invention for interaction with cancer cells. FIG. 3 shows an image taken of stabilized, biocompatible gold nanoparticles internalized in cancer cells. The internalization of nanoparticles may be mediated through endosomal uptake by cells.

Stabilized, biocompatible gold nanoparticles were produced in separate experiments using tea, turmeric and cinnamon. Details of the conditions used in the experiments are shown in Table 1.

TABLE 1

Gold Nanoparticle Production Processes (Examples provided here are for 1-2 Liter scale)

| | Tea | Turmeric | Cinnamon |
|---|---|---|---|
| Solvent | Water | Water | Water |
| Process time | Less than 1 min | 2 minutes | 15 minutes |
| Reaction temperature | Room Temperature | Room Temperature | Room Temperature |
| Size | 5-10 nm | 7-12 nm | 10-15 nm |
| Stability | High | High | Moderate |
| Reproducibility | High | High | High |
| Biocompatibility | Suitable for in vivo | Suitable for in vivo | Suitable for in vivo |
| Eco friendly | Zero-chemicals used | Zero-Chemicals used | Zero-Chemicals used |
| Scalability | Up to 2 liter | Up to 1 liter | Up to 1 liter |

Sodium tetrachloroaurate and aurochloric acid used in the experiments were obtained from Aldrich Chemicals and used without further purification. Turmeric, Cinnamon and Black Tea were obtained from several geographic locations. Organic forms of these spices were obtained from authentic growers.

Synthesis Using Black Tea

Gold nanoparticles were prepared by suspending 120 mg of Black Tea in 6 ml of doubly ionized (DI) water. To this suspension 0.1 ml of 0.1M $NaAuCl_4$ solution was added. The color of the solution changes from light yellow to dark purple within 10-30 minutes indicating the formation of gold nanoparticles. The reaction is complete in 4-6 hours. The reaction can be expedited by heating. For example, the contents can be heated via in microwave heating for 5-10 seconds. The pH of the solution after reaction is 3-4 and can be adjusted to physiological pH by adding 0.1 ml of phosphate buffer concentrate (pH 7) to whole volume. The nanoparticles generated by using Tea were found to be stable for over a period of 4 weeks. Further stabilization of gold nanoparticles generated from Tea was achieved by adding 0.2 ml of gum Arabic solution.

Figure 4:
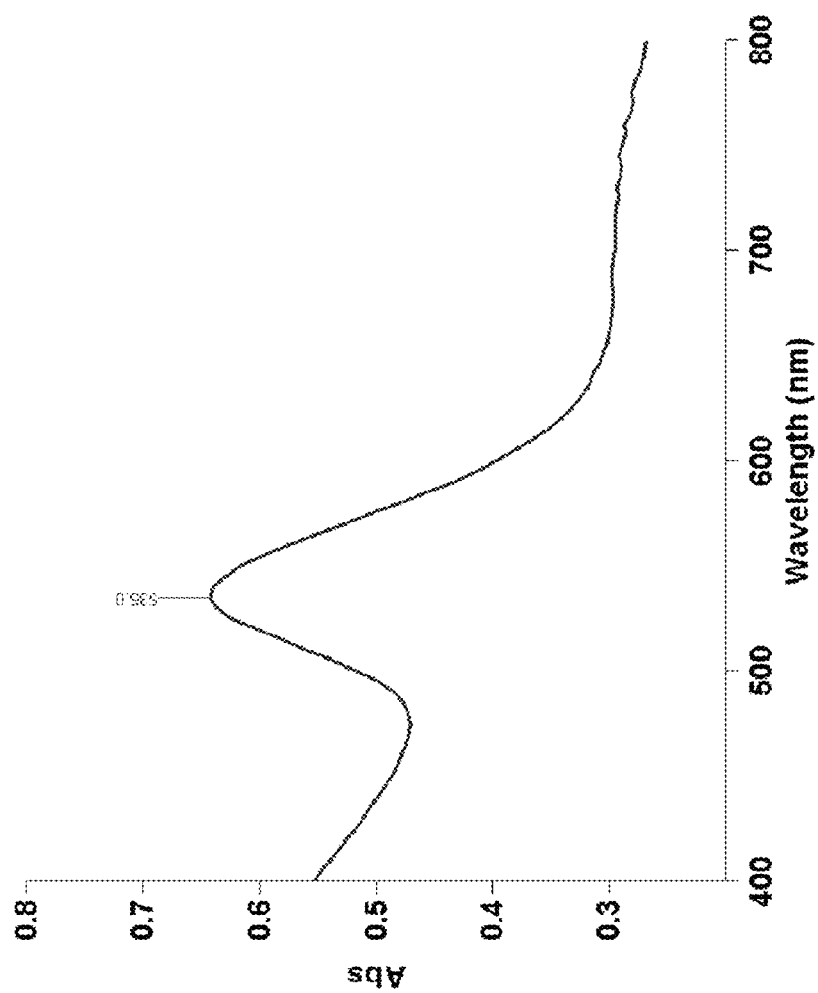
FIG. 4 is a measured UV-visible spectrum of stabilized, biocompatible gold nanoparticles of the invention produced in experiments with a coating generated by black tea.

The formation of stabilized, biocompatible gold nanoparticles using black tea was confirmed by taking the UV-visible spectrum of gold nanoparticles generated and stabilized by black tea, which is shown in FIG. 4. FIG. 4 shows the characteristic plasmon resonance band of gold nanoparticles in the ultra violet spectrum. Scanning electron micrographs also revealed the formation of stabilized, biocompatible gold nanoparticles.

In vitro stability studies were performed by challenging 0.5 ml of black tea stabilized gold nanoparticle solutions in aqueous media with 0.5 ml each of 0.2M Cysteine, 0.2M Histidine and 0.2M Human Serum Albumin (HSA) solutions. The stability and the identity of the black tea stabilized gold nanoparticles were measured by recording UV absorbance at 2 hrs through 7 days. The plasmon resonance band at 535 nm confirmed the retention of nanoparticulates in all the above mixtures. Additionally, in vitro stability measurements included challenging 0.5 ml of black tea stabilized gold nanoparticles in aqueous media with 0.5 ml of 35% saline, TEM measurements inferred the retention of the nanoparticulate composition in all the above in vitro studies

Synthesis Using Turmeric

Stabilized, biocompatible gold nanoparticles were also prepared by suspending 100 mg of turmeric in 61 ml of doubly ionized (DI) water. To this suspension 0.1 ml of 0.1M $NaAuCl_4$ solution was added. The color of the solution changes from light yellow to dark purple within 10-30 minutes indicating the formation of turmeric stabilized gold nanoparticles. The reaction is complete in 4-6 hours. The reaction can be expedited by heating. Heating can be conducted, for example, by heating the contents in microwave for 5-10 seconds. The pH of the turmeric stabilized gold nanoparticle solution is 3-4 and can be adjusted to physiological pH by adding 0.1 ml of phosphate buffer concentrate (pH 7) to whole volume. The nanoparticles generated using turmeric are stable for over a period of 4 weeks. Further stabilization of gold nanoparticles generated from turmeric was achieved by adding 0.2 ml of gum Arabic solution.

Figure 5:
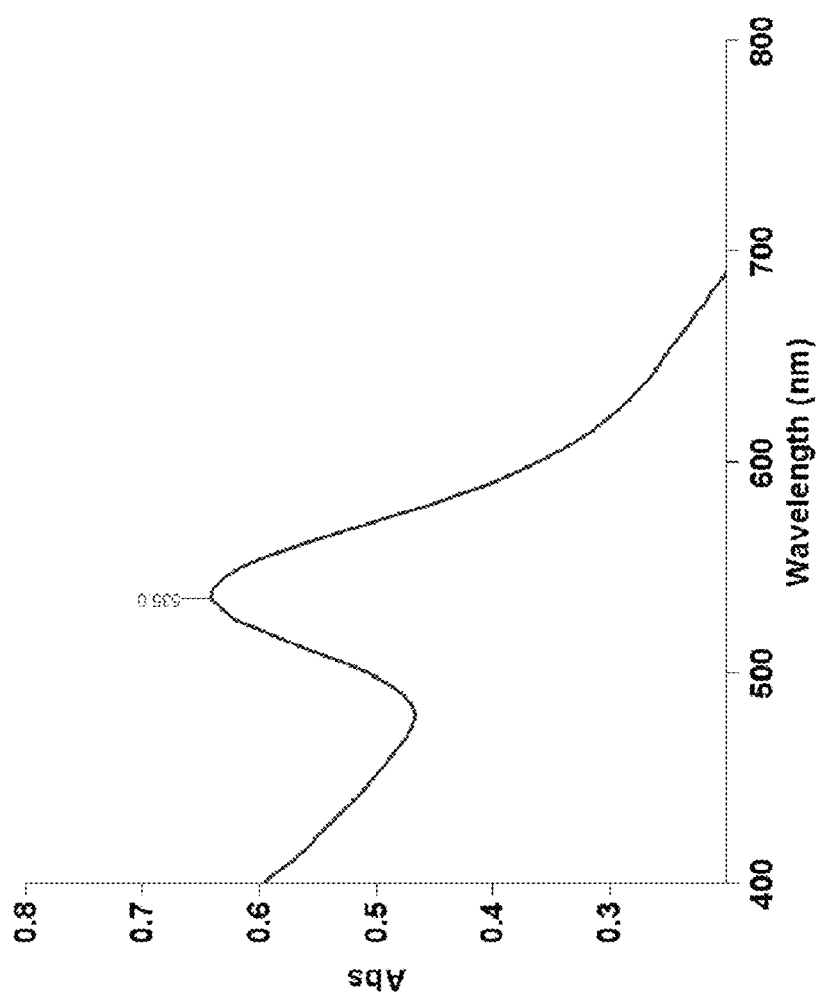
FIG. 5 is a measured UV-visible spectrum of stabilized, biocompatible gold nanoparticles of the invention produced in experiments with a coating generated by turmeric.

The formation of stabilized, biocompatible gold nanoparticles using turmeric was confirmed by taking the UV-visible spectrum of gold nanoparticles generated and stabilized by black tea, which is shown in FIG. 5. FIG. 5 shows the characteristic plasmon resonance band of gold nanoparticles in the ultra violet spectrum. Scanning electron micrographs also revealed the formation of stabilized, biocompatible gold nanoparticles.

In vitro stability studies were performed by challenging 0.5 ml of turmeric stabilized gold nanoparticle solutions in aqueous media with 0.5 ml each of 0.2M Cysteine, 0.2M Histidine and 0.2M Human Serum Albumin (HSA) solutions. The stability and the identity of turmeric stabilized gold nanoparticles were measured by recording UV absorbance at 2 hrs through 7 days. The plasmon resonance band at 535 nm confirmed the retention of nanoparticulates in all the above mixtures. Additionally, in vitro stability measurements included challenging 0.5 ml of turmeric stabilized gold nanoparticle solutions in aqueous media with 0.5 ml of 35% saline. TEM measurements inferred the retention of the nanoparticulate composition in all the above in vitro studies.

Synthesis Using Cinnamon

Stabilized, biocompatible gold nanoparticles were prepared by suspending 50 mg of Cinnamon in 6 ml of doubly ionized (DI) water. To this suspension 0.1 ml of 0.1M $NaAuCl_4$ solution was added. The color of the solution changes from light yellow to dark purple within 10-30 minutes indicating the formation of cinnamon stabilized gold nanoparticle. The reaction is complete in 4-6 hours. The reaction can be expedited by heating, such as by microwave heating. The pH of the cinnamon stabilized gold nanoparticle solution is 3-4 and can be adjusted to physiological pH by adding 0.1 ml of phosphate buffer. The cinnamon stabilized gold nanoparticles are stable or over a period of 4 weeks. Further stabilization can be achieved by adding 0.2 ml of gum Arabic solution.

Figure 6:
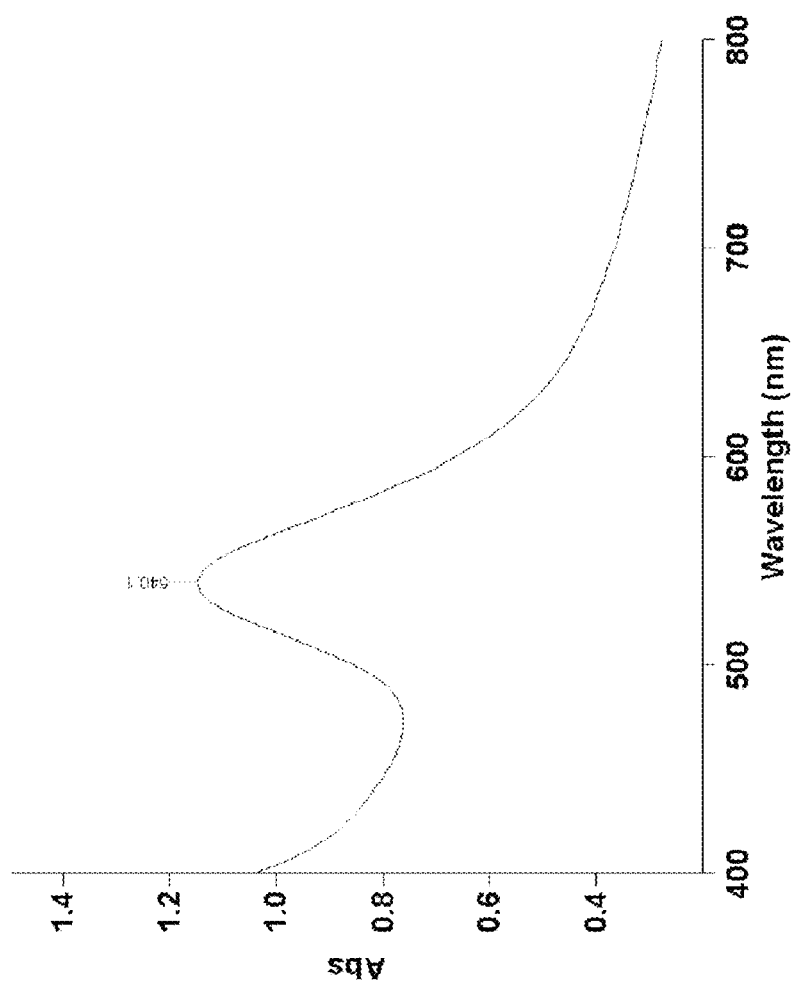
FIG. 6 is a measured UV-visible spectrum of stabilized, biocompatible gold nanoparticles of) the invention produced in experiments with a coating generated by cinnamon.

The formation of stabilized, biocompatible gold nanoparticles using cinnamon was confirmed by taking the UV-visible spectrum of gold nanoparticles generated and stabilized by cinnamon, which is shown in FIG. 6. FIG. 6 shows the characteristic plasmon resonance band of gold nanoparticles in the ultra violet spectrum. Scanning electron micrographs also revealed the formation of stabilized, biocompatible gold nanoparticles.

In vitro stability studies were performed by challenging 0.5 ml of cinnamon stabilized gold nanoparticles in aqueous media with 0.5 ml each of 0.2M Cysteine, 0.2M Histidine and 0.2M Human Serum Albumin (1-SA) solutions. The stability and the identity of cinnamon stabilized gold nanoparticles were measured by recording UV absorbance at 2 hrs through 7 days. The plasmon resonance band at 535 nm confirmed the retention of nanoparticulates in all the above mixtures. Additionally, in vitro stability measurements included challenging 0.5 ml of cinnamon stabilized gold nanoparticles in aqueous media with 0.5 ml of 35% saline. TFM measurements inferred the retention of the nanoparticulate composition in all the above in vitro studies.

Synthesis Using Tea and Various Conditions

Stabilized, biocompatible stabilized gold nanoparticles were prepared under various conditions using Tea. In the additional Tea experiments, the $NaAuCl_4$ gold salt was procured from Alfa-Aesar. Average size and size distribution of stabilized gold nanoparticles synthesized were determined by processing of TEM images. Absorption measurements were made using a Varian Cary 50 UV-Vis spectrophotometers with 1 mL of stabilized gold nanoparticle solution in disposable cuvettes of 10 mm path length. The various particles in the additional experiments will be designated with numerical extensions, e.g., −1, −2, −3 . . . .

Tea Initiated and Stabilized Gold Nanoparticles (T-AuNP-1)

To a 10 mL, vial was added 6 mL of doubly ionized water (DI), followed by the addition of 100 mg of Tea (Darjeeling Tea). The reaction mixture was stirred continuously at 25° C. for 1.5 min. To the stirring mixture was added 100 µL of 0.1M $NaAuCl_4$ solution (in DI water). The color of the mixture turned purple-red from pale yellow within 5 minutes after the addition indicating the formation of stabilized gold nanoparticles. The reaction mixture was stirred for an additional 15 minutes. The stabilized gold nanoparticles thus formed were separated from residual tea leaves immediately using a 5 micron filter and were characterized by UV-Vis absorption spectroscopy and TEM analysis.

Tea Initiated and Gum Arabic Stabilized Gold Nanoparticles (T-AuNP-2)

To a 10 mL vial was added 0.012 g of Gum Arabic, 6 mL, of doubly ionized water (DI), followed by the addition of 100 mg of Tea (Darjeeling Tea). The reaction mixture was stirred continuously at 25° C. for 15 min. To the stirring mixture was added 100 µL of 0.1M $NaAuCl_4$ solution (in DI water). The color of the mixture turned purple-red from pale yellow within 10 minutes indicating the formation of stabilized gold nanoparticles. The reaction mixture was stirred for an additional 15 minutes. The stabilized gold nanoparticles thus formed were separated from residual tea leaves immediately using a 5 micron filter and were characterized by UV-Vis absorption spectroscopy and TEM.

Tea Initiated and Stabilized Gold Nanoparticles at 40° C. (T-AuNP-3)

To a 10 mL, vial was added 6 mL of doubly ionized water (DI), followed by the addition of 100 mg of Tea (Darjeeling Tea). The reaction mixture was stirred continuously at elevated temperature (~40° C.) for 5 min. To the warm stirring mixture was added 100 µL of 0.1M $NaAuCl_4$ solution (in DI water). The color of the mixture turned purple-red from, pale yellow instantly indicating the formation of stabilized gold nanoparticles. The reaction mixture was stirred for an additional 5 minutes. The stabilized gold nanoparticles in DI water were separated from residual tea leaves immediately using a 5 micron filter and were characterized by UV-absorption spectroscopy and TEM analysis.

Tea Initiated and Gum Arabic Stabilized Gold Nanoparticles at 40° C. (T-AuNP-4)

To a 10 mL vial was added 0.012 g of gum Arabic, 6 mL of doubly ionized water (DI), followed by the addition of 100 mg of Tea (Darjeeling Tea). The reaction mixture was stirred continuously at elevated temperature (~40° C.) for 5 min. To the warm stirring mixture was added 100 μL of 0.1M NaAuCl$_4$ solution (in DI water). The color of the mixture turned purple-red from pale yellow in about 5-10 min indicating the formation of stabilized gold nanoparticles. The reaction mixture was stirred for 5 more minutes. The stabilized gold nanoparticles in DI water were separated immediately using a 5 micron filter. The tea/gum Arabic stabilized gold nanoparticles (T-AuNP-4) were characterized by UV-absorption spectroscopy and TEM analysis.

Tea Extract (>80% Theaflavins) Initiated/Stabilized Gold Nanoparticles (Tea-AuNP-5)

To a 20 mL vial was added 0.035 g of Tea extract (>80% theaflavins; Sigma), 6 mL of doubly ionized water (DI). The reaction mixture was stirred continuously at 25° C. for 3 min. To the stirring mixture was added 100 μL of 0.1M NaAuCl$_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by IV-Vis absorption spectroscopy and TEM. Plasmon resonance band at ~540 nm indicated the formation of stabilized gold nanoparticles. TEM measurements confirmed the size distribution of stabilized gold nanoparticles.

Epicatechin Gallate Initiated/Stabilized Gold Nanoparticles (Tea-AuNP-6)

An initial experiment with EGCg was conducted. To a 20 mL vial was added 2.2 mg of Epicatechin gallate, 6 mL of doubly ionized water (DI). The reaction mixture was stirred continuously at 25° C. for 3 min. To the stirring mixture was added 100 μL of 0.1 μM NaAuCl$_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Catechin Initiated/Stabilized Gold Nano-Articles (Tea-AuNP-7)

To a 20 mL vial was added 2.2 mg of Catechin, 6 ml, of doubly ionized water (DI). The reaction mixture was stirred continuously at 25° C. for 3 min. To the stirring mixture was added 100 μL of 0.1M NaAuCl$_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Catechin Gallate Initiated/Stabilized Old Nanoparticles (Tea-AuNP-8)

To a 20 mL vial was added 2.2 mg of Catechin gallate, 6 mL of doubly ionized water (DI). The reaction mixture was stirred continuously at 25° C. for 3 rain. To the stirring mixture was added 100 μL of 0.1 μM NaAuCl$_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Epicatechin Initiated/Stabilized Gold Nanoparticles (Tea-AuNP-9)

To a 20 mL vial was added 2.2 mg of Epicatechin, 6 mL of doubly ionized water (DI). The reaction mixture was stirred continuously at 25° C. for 3 min. To the stirring mixture was added 100 μL of 0.1M NaAuCl$_4$ solution (in DI water). The color of the mixture turned purple-red From pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 mm indicated the formation of stabilized gold nanoparticles. TEM measurements confirmed the size distribution of stabilized gold nanoparticles.

Epigallocatechin Initiated/Stabilized Gold Nanoparticles (Tea-AuNP-10)

To a 20 mL vial was added 2.2 mg of Epigallocatechin, 6 mL of doubly ionized water (DI). The reaction mixture was stirred continuously at 25° C. for 3 min. To the stirring mixture was added 100 μL of 0.1M NaAuCl$_4$ solution (in DI water). The color of the mixture turned purple-red from pale yellow within minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

Epigallocatechin Gallate (EGCG) Initiated/Stabilized Gold Nanoparticles (Tea-AuNP-11)

To a 20 mL vial was added 2.2 mg of Epigallocatechin gallate, 6 mL of doubly ionized water (DI). The reaction mixture was stirred continuously at 25° C. for 3 min. To the stirring mixture was added 100 μL of 0.1M NaAuCl$_4$ solution (in DI water). The color of the mixture turned purple-red from pale yellow within 5 minutes indicating the formation of stabilized gold nanoparticles. The reaction mixture was stirred for an additional 15 minutes at 25° C. The stabilized gold nanoparticles thus obtained were characterized by UV-Vis absorption spectroscopy and TEM. Plasmon resonance band at ~535 nm indicated the formation of stabilized gold nanoparticles. TEM measurements confirmed the size distribution of stabilized gold nanoparticles.

In Vitro Stability Studies of (T-AuNP-1-4 Stabilized Gold Nanoparticles

In vitro stabilities of the four different tea-mediated stabilized gold nanoparticles (T-AuNP, 1-4) were tested in the presence of NaCl, cysteine, histidine, HSA and BSA solutions. Typically, 1 mL of stabilized gold nanoparticle solution was added to glass vials containing 0.5 mL of 5% NaCl, 0.5% cysteine, 0.2M histidine, 0.5% HSA, 0.5% BSA solutions respectively and incubated for min. The stability and the identity of stabilized gold nanoparticles (T-AuNP 1-4) were measured by recording UV absorbance after 30 min. A plasmon resonance band at ~535 nm confirmed the retention of nanoparticulates in all the above mixtures. TEM measurements inferred the retention of the nanoparticulate compositions in all the above four different gold nanoconstructs signifying robust nature of these nanoparticles under in vitro conditions.

Cellular Internalization of T-AuNPs

Minimum essential medium (MEM with nonessential amino acids, powdered), HEPES, bovine insulin, streptomycin sulfate, penicillin-G, were obtained from Sigma Chemical Company (St. Louis, Mo.); all were cell culture tested when available. Bovine calf serum, phenol red (sodium salt), and lyophilized trypsin were obtained from Gibco BRL (Grand Island, N.Y.). MCF-7 breast cancer cells and PC-3 prostate cancer cells were obtained from V. Craig Jordan, University of Wisconsin-Madison and ATCC respectively. MCF-7 cells were maintained in MEM with nonessential amino acids, 10 pg/ml phenol red, 10 mM HEPES, 6 ng/ml insulin, 100 units/ml penicillin, 100 pg/ml streptomycin, and 5% charcoal-stripped calf serum (maintenance medium). PC-3 cells were maintained in RPMI medium supplemented with 4.5 g/L, D-glucose, 25 mM HEPES, 0.11 g/L sodium pyruvate, 1.5 g/L sodium bi carbonate, 2 mM L-glutamine and 10% FBS and antibiotics.

Cell Internalization Studies:

About 16,000 cells were plated into each well in a 6 well plate and this plate was incubated at 37° C. for 18.0-20.0 hrs to allow the cells to recover. After the cells were recovered the media from each well was aspirated and fresh growth media was added (about 4 mL per each well). Cells were allowed to grow for 3 days changing the media every alternate day. On the $5^{th}$ day, 25 micro molar concentrations of T-AuNPs solutions were added to each well. (Note: 25 μm stabilized gold nanoparticles solution is made up with the media itself). After adding the sample, plate was incubated for 4 h at 37° C. Media was aspirated from each well after 4 h and the cell layer was rinsed with CMFH-EDTA (Calcium-Magnesium-Free-Hark's+HEPES-EDTA) solution to remove all traces of serum which contains trypsin inhibitor. About 0.5 mL of Trypsin-EDTA solution was added to each well and cells were observed under an inverted microscope until cell layer is dispersed. 4.0 mL of complete growth medium was added to each well and cells were aspirated by gently pipetting. The cell suspension was transferred into to a centrifuge tube and centrifuged at approximately 125×g for 5 to 10 minutes. The cells were washed thoroughly with chilled PBS, pelleted by centrifugation and fixed with 0.1M Na-Cacodylate buffer containing 2% glutaraldehyde and 2% paraformaldehyde. The pellets were post fixed with 1% osmium tetraoxide, dehydrated and embedded in Epon/Spurr's resin and 80 nm sections were collected and placed on TEM grids followed by sequential counter staining with urenyle acetate and lead citrate. TEM grids were observed under TEM (Joel 1400) and images were recorded at different magnifications.

Cytotoxicity Evaluations

MTT Cell Proliferation Assay kit was obtained from ATCC. For the cytotoxicity evaluation of these nanoparticles, MTT assay was done as described by supplier. Briefly, $1\times10^5$ cells/ml cells at the exponential growth phase were taken in a flat-bottomed 96-well polystyrene-coated plate and were incubated for 24 h in $CO_2$ incubator at 5% $CO_2$ and 37° C. Series of dilutions like 10, 25, 50, 100, and 150 μM of T-AuNP-1 were made in the medium. Each concentration was added to the plate in quadruplet manner. After 24 h of incubation, 10 μl/well MTT (stock solution 5 mg/ml PBS) was added for 6 h and formazan crystals so formed were dissolved in 10 μl detergent. The plates were read in a microplate reader (Dynastic MR 5000, USA) operating at 570 nm. Wells with complete medium, nanoparticles, and MTT, but without cells were used as blanks. All experiments were performed 3 times in quadruplets, and the average of all of the experiments has been shown as cell-viability percentage in comparison with the control experiment, while gold untreated controls were considered as 100% viable.

Characterization of the Tea Stabilized Gold Nanoparticles Under Various Conditions Absorption measurements indicated that the plasmon resonance wavelength, $\lambda_{max}$ of various T-AuNPs is ~535 nm. The sizes of T-AuNPs are in the range of 15-42 nm as measured from TEM techniques The phenolics and other phytochemicals within tea not only result in effective reduction of gold salts to their corresponding nanoparticles but their chemical framework wrap around the stabilized gold nanoparticles to provide excellent robustness against agglomeration.

Size and Morphology:

TEM measurements on T-AuNPs 1-4 show that particles are spherical in shape within the size range of 16-35 nm. Size distribution analysis of T-AuNPs confirm that particles are mono disperse. DCS technique measures size of the nanoparticle by determining the time required for nanoparticles to traverse a sucrose density gradient created in a disc centrifuge. Both the techniques, TEM and DCS, provide sizes of metallic-gold cores. Gold nanoparticulate sizes measured by TEM and DCS, were in good agreement and are in the range 16-35 nm. Dynamic light scattering was employed to calculate the size of gold coated with phytochemicals (hydrodynamic radius). The tea phytochemicals coatings on stabilized gold nanoparticles are expected to cause substantial changes in the hydrodynamic radius of T-AuNPs. Hydrodynamic diameter of T-AuNP-1 and T-AuNP-2 as determined from DLS measurements gave a values of 105±1 and 165±1 respectively, suggesting that tea phytochemicals (catechins, theaflavins and thearibigins) are capped on stabilized gold nanoparticles. The measurement of charge on nanoparticles, Zeta Potential (ζ), provides crucial information on the stability of the nanoparticle dispersion. The magnitude of the measured zeta potential is an indication of the repulsive forces that are present and can be used to predict the long-term stability of the nanoparticulate dispersion. The stability of nanoparticulate dispersion depends upon the balance of the repulsive and attractive forces that exist between nanoparticles as they approach one another. If all the particles have a mutual repulsion then the dispersion will remain stable. However, little or no repulsion between particles, lead to aggregation. Negative zeta potential of −32±1 and −25±1 for T-AuNP-1 and T-AuNP-2 indicates that the particles repel each other and there is no tendency or the particles to aggregate.

Large Scale Synthesis Optimization

Synthetic conditions have been optimized for the quantitative large scale conversions of $NaAuCl_4$ to the corresponding AuNPs using tea leaves. The nature and chemical roles of different phytochemicals in tea leaves for the production of T-AuNPs are summarized in the following sections. The main phytochemicals present in black tea leaves consist of water soluble Catechins (Catechin, Epicatechin, Epicatechin gallate, Epigallocatechin, Epigallocatechin gallate etc.,), Theaflavins (Theaflavin, Theaflavin 3-gallate, Theaflavin 3'-gallate, Theaflavin 3,3'-gallate etc.,) and Thearubigins, which are oligomers of catechins of unknown structure. Generation of T-AuNPS using tea leaves involves aqueous media. Experiments have systematically investigated the roles of catechins and theaflavins for the generation and stabilization of AuNPs.

Role of Catechins

The series of independent experiments for the generation of stabilized gold nanoparticles using commercially available catechins (Catechin, Epicatechin, Epicatechin gallate, Catechin gallate, Epigallocatechin, Epigallocatechin gallate)

provide the necessary information to confirm that catechins are excellent reducing and stabilizing agents to reduce Au(III) to stabilized gold nanoparticles. The reactions went to completion within 30 min. Absorption measurements indicated that the plasmon resonance wavelength, $\lambda_{max}$, T-AuNPs are ~530 nm. The size of the T-AuNPs is found to be 15-52 nm as measured from the TEM images. The gold nanoparticles obtained using catechin, and epigallocatechin gallate (EGCG) showed excellent stability which was conformed by their in vitro stability studies. The stabilized gold nanoparticles obtained using epigallocatechin and epicatechin showed minimum stability, thus generating the formation of brown suspensions. To further investigate the reduction potential of all the catechins, the formation of stabilized gold nanoparticles using gum Arabic (a glyco protein) as stabilizer was also tested. The experiments revealed that all the catechins (Catechin, Epicatechin, Epicatechin gallate, Epigallocatechin, Catechin gallate, Epigallocatechin gallate) act as excellent reducing agents to reduce the Au(III) to stabilized gold nanoparticles. The nanoparticles thus generated showed improved stability against various salts and serum proteins. The experiments unambiguously uncover that catechin and epigallocatechin gallate (EGCG) have excellent reducing and stabilizing capabilities to reduce and stabilize the stabilized gold nanoparticle.

(ii) Role of Tea Extract (>80% Theaflavins)

The role of theaflavins in the generation of stabilized gold nanoparticles was also investigated. The tea extract in these experiments was from Sigma-Aldrich and contained >80% theaflavins. Addition of aqueous solution of NaAuCl$_4$ to the theaflavin aqueous solution at 25° C. resulted in the formation of purple colored solutions within 30 minutes. The stabilized gold nanoparticles thus obtained by using theaflavin were characterized by UV-Vis absorption spectroscopy and TEM. Plasmon resonance band at ~535 nm indicated the formation of stabilized gold nanoparticles. TEM measurements confirmed the size distribution of stabilized gold nanoparticles. Detailed in vitro stabilities of the stabilized gold nanoparticles confirmed that the nanoparticles are extremely stable under various conditions. These results convincingly demonstrate the reducing and stabilizing capabilities of mixture of theaflavins. The determination of unambiguous roles of catechins and theaflavins will find applications in careful design of tumor specific imaging modalities.

The reservoir of non toxic phytochemicals in tea serves as a source of non toxic reducing agents with capabilities for in vivo administrations in situations that require generation of stabilized gold nanoparticles under in vivo conditions. The approach to gold nanoparticulate synthesis in the various tea experiments provides a universally applicable generalized synthetic route using phytochemicals available in tea and can provide for the fabrication of a library of stabilized gold nanoparticles with various non-toxic bioconjugates. One such example has been explored via the utilization of gum Arabic (GA), a commonly used non-toxic food additive. The example use of gum Arabic protein shows that bioconjugates can be used as a green platform to achieve excellent control over size and shape of nanoparticles.

The additional envirofriendly component, in the form of gum Arabic, also provides additional advantages. The use of gum Arabic along with Tea leaves resulted in an increase in the optical density (absorbance) in the UV-Vis spectra of reaction mixtures. This observation demonstrates that gum Arabic is likely serving as a biochemical platform to drive such reactions to completion with consequent production of well defined and uniform spherical stabilized gold nanoparticles. The effect of temperature on the formation of stabilized gold nanoparticles revealed that nanoparticle formation at elevated temperatures results in a randomly distributed spherical stabilized gold nanoparticles of sizes varying from 15-30 nm.

An issue of critical importance for in vivo imaging applications is the stability of AuNPs over a reasonable time period. The stability of T-AuNPs evaluated by monitoring the plasmon ($\lambda$max) in 0.5% Cysteine, 0.2M Histidine, 0.5% Human Serum Albumin (HSA), 0.5% Bovine Serum Albumin (BSA) or 5% NaCl solutions were evaluate over 30 min. The stability of T-AuNPs in pH 5, 7 and pH 9 phosphate buffer solutions was also tested. The plasmon wavelength in all the above formulations shifts ~1-5 nm, showing that the AuNPs are intact and that they demonstrate excellent in vitro stability in biological fluids at physiological pH For biomedical applications that require lower concentrations of AuNPs, it is vitally important that dilutions of AuNP solutions do not alter their characteristic chemical and photophysical properties. The effect of dilution on the stability of T-AuNPs under dilution was measured. Specifically, the plasmon resonance wavelength ($\lambda$max) was monitored after successive addition of 0.1 mL of doubly ionized (DI) water to 1 mL of AuNP solutions. The absorption intensity at $\lambda$max was found to be linearly dependent on the concentration of AuNPs, in accordance with Beer Lambert's law. The $\lambda$max of AuNPs did not change at very dilute conditions.

Cellular internalization studies was studied via incubation of aliquots of T-AuNPs with cancer cells. TEM images of prostate (PC-3) and breast tumor (MCF-7) cells post treated with T-AuNPs showed significant internalization of nanoparticles via endocytosis within the MCF-7 and PC-3 cells. The internalization of nanoparticles within cells could occur via processes including phagocytosis, fluid-phase endocytosis, and receptor-mediated endocytosis. The viability of both PC-3 and MCF-7 cells post internalization of T-AuNPs suggests that the phytochemical coating renders the nanoparticles to be non toxic to cells. Such internalization of stabilized gold nanoparticles, keeping the cellular machinery intact provides new opportunities for probing cellular processes via nanoparticulate-mediated imaging.

The cytotoxicity of T-AuNPs under in vitro conditions in Prostate (PC-3) and Breast (MCF-7) cancer cells were examined in terms of the effect of stabilized gold nanoparticles on cell proliferation by the MT assay. Untreated cells as well as cells treated with 10, 25, 50, 100, and 150 µM concentrations of stabilized gold nanoparticles for 24 h were subjected to the MTT assay for cell-viability determination. In this assay, only cells that are viable after 24 h exposure to the sample are capable to metabolize a dye (3-(4,5-dimethylthiazol-2-yl)-2, 5-diphenyltetrazolium bromide) efficiently and produce a purple coloured precipitate which is dissolved in a detergent and analyzed sphectrophotometrically. After 24 h of post treatment, PC-3, MCF-7 cells showed excellent viability even up to 1.50 µM concentrations of T-AuNP These results demonstrate that the phytochemicals within tea provide a non toxic coating on stabilized gold nanoparticles and corroborate the results as seen in the internalization studies discussed above. It is also important to recognize that a vast majority of Gold (I) and Gold (III) compounds exhibit varying degrees of cytotoxicity to a variety of cells. The lack of any noticeable toxicity of T-AuNPs provides new opportunities for the safe delivery and applications of such nanoparticles in molecular imaging and therapy.

Additional Characterization and Testing of Cinnamon Stabilized Gold Nanoparticles Fabricated at Various Conditions For additional characterization, of cinnamon stabilized gold nanoparticles, NaAuCl$_4$ was purchased from Alfa-Aesar. Trans-cinnamaldehyde, eugenol, cinnamyl acetate, cinnamyl alcohol, linalool, α-terpinene, (R)-(+)-Limonene, eugenyl acetate, linalyl acetate, catechin, epicatechin were purchased from Sigma (St. Louis, Mo.), All cell culture materials e.g. minimum essential medium (MEM with nonessential amino acids, powdered), HEPES, bovine insulin, streptomycin sulfate, penicillin-G, were obtained from Sigma (St. Louis, Mo.). Bovine calf serum, phenol red (sodium salt), and lyophilized trypsin were obtained from Gibco BRL (Grand Island, N.Y.).

Synthesis of Cinnamon Stabilized Gold Nanoparticles at Room Temperature (27-3° C.).

To a 20 mL vial was added 6 mL of doubly ionized (DI) water followed by the addition of 25 mg of cinnamon. The mixture was stirred continuously at 25° C. for 5 min. To the stirring mixture was added 100 μL of 0.1M. $NaAuCl_4$ solution (in DI water). The color of the mixture turned purple within minutes after the addition of $NaAuCl_4$ indicating the formation of gold nanoparticles. The reaction mixture was stirred for an additional 10 minutes. The gold nanoparticle solution was separated from the residual cinnamon powder by means of a standard paper filter. The solution was further filtered through a 0.5 micron filter. Finally, the gold nanoparticles were characterized by UV-Vis absorption spectroscopy and TEM analysis.

Generation of Gold Nanoparticles by Individual Cinnamon Phytochemicals in Starch.

Attempted synthesis of gold nanoparticles from $NaAuCl_4$ was done with each of major components present in cinnamon as phytochemicals. Except linalool and catechin compounds, all other components have failed to produce nanoparticles by reducing $NaAuCl_4$. Starch, present as carbohydrate (80-90%) in cinnamon is used to stabilize the gold nanoparticles during the reduction process. The procedure of making gold nanoparticles by linalool and catechin compounds in starch is as follows: To a 20 mL vial was added 6 mL of doubly ionized (DI) water followed by the addition of 22.5 mg of starch. The mixture was stirred continuously at ~80° C. for 10 min. After dissolving the starch, the solution was cooled down to ~30° C. with continuous stirring at room temperature. To this solution was added 10 mg of linalool or 5 mg catechin or 5 mg epicatechin followed by 100 μL of 0.1M $NaAuCl_4$ solution (in DI water). The color of the mixture turned purple-red within 30 minutes after the addition of $NaAuCl_4$ indicating the formation of gold nanoparticles. The solution was finally characterized by UV-Vis absorption spectroscopy and TEM analysis.

In Vitro Stability Studies of Cinnamon & Cinnamon Component Stabilized Gold Nanoparticles.

In vitro stability studies were performed by mixing gold nanoparticles to aqueous solutions of 10% NaCl, 0.5% cysteine, 0.2M histidine, 0.5% HAS and 0.5% BSA. The stability of the conjugates was measured by monitoring the UV absorbance over the periods 30 min, 2 hrs and 7 days. A negligible change in plasmon band was observed in UV which confirmed the retention of nanoparticulate composition in all of the mixtures. TEM studies also inferred the stability of the nanoparticles in all of the in vitro studies.

Cell Culture of Cinnamon & Cinnamon Component Stabilized Gold Nanoparticles.

Human fibroblasts primary cultures were obtained from the Bond Life Science Centre at University of Missouri-Columbia. Fibroblast cells were maintained in DMEM with 10 $pgmL^{-1}$ phenol red, 10 mM HEPES, 100 units $mL^{-1}$ penicillin, 100 $pgmL^{-1}$ streptomycin, and 10% donor bovine serum (maintenance medium).

In Vitro Cytotoxicity Measurements (MTT Assay) of Cinnamon & Cinnamon Component Stabilized Gold Nanoparticles.

The in vitro cytotoxicity evaluation of cinnamon stabilized gold nanoparticles was performed as described by the supplier (ATCC, USA). Briefly, $2\times10^4$ fibroblasts cells at the exponential growth phase were seeded in each well of a flat-bottomed 96-well polystyrene-coated plate and were incubated at 37° C. for 24 h in $CO_2$ incubator at 5% $CO_2$ environment. Series of dilutions like 25, 50, 125 and 165 μM (gold atoms) of these nanoparticles were made in the medium. Each concentration was added to the plate in pentaplet manner. After 24 h incubation, 10 μL, per well MTT (stock solution 5 $mgmL^{-1}$ PBS) (ATCC, USA) was added for 24 h and formosan crystals so formed were dissolved in 100 μL detergent. The plates were kept for 18 h in dark at 25° C. to dissolve all the crystals and the intensity of developed color was measured by micro plate reader (Dynastic MR 5000, USA) operating at 570 nm wavelength. Wells with complete medium, nanoparticles, and MTT, but without cells were used as blanks. Untreated cells were considered 100% viable.

Cellular Uptake of Cinnamon & Cinnamon Component Stabilized Gold Nanoparticles.

MCF-7 breast cancer and PC-3 prostate cancer cells obtained from ATCC were used for the in-vitro cell internalization analyses. MCF-7 cells were maintained in MEM with nonessential amino acids, 10 pg/ml phenol red, 10 mM HEPES, 6 ng/ml insulin, 100 units/ml penicillin, 100 pg/ml streptomycin, and 10% FBS (maintenance medium). PC-3 cells were maintained in RPMI medium supplemented with 4.5 g/L D-glucose, 25 mM HEPES, 0.11 g/L sodium pyruvate, 1.5 g/L sodium bi carbonate, 2 mM L-glutamine and 10% FBS and antibiotics. Known concentration of cinnamon stabilized gold nanoparticles (100 μg/mL) were added to each type of cells (~10000 cells) and incubated for 4 h at 37° C. Following incubation, cells were washed three times with PBS, centrifuged into small pellets, and fixed with 2% glutaraldehyde 2% paraformaldehyde in sodium cacodylate buffer (0.1M). The cells were further fixed with 1% buffered osmium tetraoxide and dehydrated in an ethanol series before embedding in Epon-Spurr epoxy resin. Sections (75-85 nm) were cut using Leica Ultracut UCT ultramicrotome and placed on a TEM grid. The sections were post-stained with uranyl acetate and lead citrate for organelle visualization. The prepared samples were viewed with JEOL 1400 Transmission Electron Microscope.

Biodistribution of Cinnamon & Cinnamon Component Stabilized Gold Nanoparticles in TRAMP Mice Model.

The biodistribution of Cin-AuNPs were assessed in two groups of TRAMP mice weighing ~20 g. The measurements were done by considering the amount of gold in various organs using AAS. For each time point, the animals were intravenously injected though tail with Cin-AuNP (200 μL, 3.75 mg/mL) and sacrificed after 4 h and 24 h time periods. The amount of gold in blood, brain, heart, kidney, muscle, pancreas, tumor, spleen, lung, liver and tail were determined to assess the tissue affinity for Cin-AuNPs. After 4 h of dosing, the average gold concentrations were negligible in blood, brain heart, kidney, muscle, pancreas and tumor while a very small amount of gold was observed in liver (65.0-77.0 μg/g of tissue) and tail (28.0-31.0 μg/g of tissue). The highest gold concentration was observed in lung (~482.0 μg/g of tissue). At 24 h after dosing, the gold concentrations remaining in the lung were not significantly different from those after 4 h, which suggests a good affinity of the AuNPs for lung tissues.

Sample Preparation for AAS.

Tissues were removed from −80° C. storage and allowed to partially thaw. Following partial thawing whole tissue samples were placed in a 15 ml clean graduated centrifuge tube with concentrated trace metal grade nitric acid (Fisher Scientific) and concentrated trace metal grade hydrochloric acid in 1:2 ratio and heated in an oven to 85° C. overnight (12-18 hr). The amount of acid depended on the weight of the tissue and the proportion used was 1 mg (tissue): 1 µL ($HNO_3$): 0.5 µL (HCl). After cooling, the digest was diluted in 1:10 ratio with ultra pure water for analysis. The mouse carcasses were homogenized by grinding into a fine powder using a stein mill and then ~1 g aliquots were digested and analyzed with the method described for the other mouse tissues.

AAS Analysis. All the samples were analyzed by furnace AAS using a standard curve spanning 0-100 micro grams/L. The furnace parameters were as specified in the user's manual for the Perkin—Elmer Analyst 800 ThGA graphite furnace. Quality-control materials (duplicates, spikes, and instrument-calibration verification) were within appropriate ranges.

CT Imaging

A Gammex/RMI Model 461 phantom was scanned using a Siemens volume zoom CT system. Five 5.0-mL glass vials containing aqueous solutions of various concentrations of Cin-AuNPs were placed in holders in the phantom. This arrangement presented a tissue like (solid water) background with Cin-AuNP contrast inclusions. Scans were performed at tube voltages of 80 and 140 kVp at the same level in the phantom. Images were reconstructed, in 4-mm-thick slices with a field of view of 208 nm. Evaluation of the contrast enhancement contribution of Cin-AuNPs was carried out by loading the digital CT images in a standard display program and then selecting a region of interest on the resultant CT image for each sample and the background. Contrast enhancement was determined in ΔHU for each mass concentration of Cin-AuNPs and each tube voltage.

Results Regarding Cinnamon & Cinnamon Component Stabilized Gold Nanoparticles.

The cinnamon stabilized gold nanoparticles (Cin-AuNP) were prepared by simple mixing of an aqueous solution of commercially available sodium tetrachloroaurate with cinnamon present in DI water. The reaction produced a purple-red color solution within 25 minutes at room temperature stirring. The absorbance profile revealed ad plasmon resonance wavelength $\lambda_{max}$ that appeared at ~540 nm. Other physicochemical properties, such as size, charge, and morphology of Cin-AuNPs were determined by transmission electron microscopy (TEM), differential centrifugal sedimentation (DCS, Disc Centrifuge, CPS Instruments), and dynamic light scattering (DLS). TEM and CPS were used to determine the core size of while DLS was used to evaluate the hydrodynamic size of phytochemicals coated gold nanoparticles. The TEM images showed the size and shape of the nanoparticles to be homogeneous with an average diameter of 13±5 nm and a narrow size distribution. As expected, the hydrodynamic size of cinnamon coated gold nanoparticles is greater than the core size measured by TEM and CPS. The negative zeta potential (ζ) value (−31.0 mV) was determined for the Cin-AuNPs which provides the necessary repulsive forces for the particles to remain stable in solution.

The main phytochemicals present in cinnamon consist of essential oil (trans-cinnamaldehyde, eugenol, linalool, trans-cinnamic acid, terpenes and others; 1-4% by weight), polyphenols (catechin, epicatechin, anthocyanidin, catecin/epicatechin oligomers, kaempferitrin and others; 5-10% by weight) and carbohydrates (starch, polysaccharides, ash; 80-90% by weight). The phenolic compounds are known as potent antioxidants and thus, may play a major role in the overall reduction of $NaAuCl_4$. The systematically investigation revealed the roles of these phytochemicals for the generation and stabilization of AuNPs by interactions with $NaAuCl_4$ in aqueous media. Experiments with individual components did not result in gold nanoparticles production except linalool and catechin compounds. Both linalool and catechin compounds are therefore able to reduce $NaAuCl_4$ in aqueous media to produce purple-red solution of AuNPs. The chemical constitution of linalool and catechin compounds, used in generating the AuNPs comprises alcoholic —OH functional group which might be responsible for the reduction of the $NaAuCl_4$. The stabilization property for AuNPs was provided only by catechin. The antioxidant catechin uniquely showed both reducing and stabilization properties simultaneously during the nanoparticle formation.

The production of gold nanoparticles did not happen in the presence of any carbohydrates present in cinnamon at room temperature (~27-30° C.). Although the formation of AuNPs was observed with glucose, arabinose, galactose, rhamnose at elevated temperatures (~80° C.), the stability was not sufficient to hold the nanoparticles in solution for significant length of time. However, when this reaction was carried out with initially dissolved starch or combination of individual carbohydrates, a similar purple-red color nanoparticle solution was obtained at room temperature with considerable stability to the AuNPs. These results unequivocally prove that while cinnamon phytochemicals are directly involved in $NaAuCl_4$ reduction, the present carbohydrates in cinnamon provide synergistic benefits to the overall reduction as well as stabilization processes.

Biomedical imaging application requires the stability of Cin-AuNP over a reasonable length of time. For this purpose, the challenging tests were performed in presence of 10% NaCl, cysteine, histidine, HSA and BSA solutions to determine the in vitro stabilities of the nano constructs in biological environments. The stability and the identity of Cin-AuNPs were measured by recording UV absorbance after 30 min. The plasmon resonance band at ~535 nm confirmed the retention of nanoparticulates in all the above mixtures. This indicates that the AuNPs are intact and thus, demonstrate excellent in vitro stability in biological fluids at physiological pH. TEM measurements also inferred the retention of the nanoparticulate compositions in all of the above different medium signifying robust nature of these nanoparticles under in vitro conditions. The stability also remain unaffected from pH 4 to 9 range, which implies that this Cin-AuNPs can be used in a wide pH range for various biomedical applications.

In vivo stability was also tested. The cytotoxicity of Cin-AuNPs was studied on primary human fibroblast cells under in vitro conditions by using a colorimetric cell-viability (MTT) assay. In the MIT assay, the cell viability was examined in terms of the absorbance of formazan (produced by the cleavage of MTT by dehydrogenases in living cells) at 570 nm which is directly proportional to the number of live cells. The experiment was performed using a wide range of concentrations of Cin-AuNPs (0, 25, 50, 125 and 165 µM (gold atoms)). The relative cell viability was ~90% for both 24 post treatment, not significantly different from the control. It has been reported that, a number of $Au^I$ and $Au^{III}$ complexes produces significant toxicity in cell culture media. In contrast, cinnamon phytochemicals coated gold nanoparticles does not show any toxicity in primary human fibroblast cultures. This observation ensures that the phytochemicals present in cinnamon effectively reduce NaAu$^{III}$Cl$_4$ in aqueous medium and provides the nontoxic surface coating for in vivo administrations in solutions.

Gold nanoparticles were also tested for their potential applications in drug delivery and intracellular imaging applications. The internalization of cinnamon phytochemicals coated gold nanoparticles in primary human fibroblast cells as well as in MCF-7 cancer cells was tested. After careful mixing of Cin-AuNPs to both cells, the gold nanoparticles incubated cells were washed vigorously using trypsin-EDTA solution followed by PBS (pH 7.4) to remove unbound gold nanorods. TEM images of Cin-AuNPs after entering into the cells showed that cinnamon phytochemicals coated gold nanoparticles are preferentially taken by both cells, cancerous as well as non-cancerous and appeared as an individual probes in the endosomes. This endosomal localization within the cells also ensures that the specific uptake of the gold is due to the receptor mediated endocytosis. Some of the nanoparticles also appeared as a large cluster outside the cell surface. The unique behaviour of Cin-AuNPs may provide new opportunities for understanding the cellular activities via nanoparticulate-mediated imaging.

The in vivo biodistribution studies following intravenous injection of the nanoparticles (3.75 mg/mL) were carried out in two groups of mice, each weighing ~20 g. Following 200 μL intravenous administrations of Cin-AuNPs, the mice were humanely sacrificed at 4 h and 24 h time periods. The collected blood and tissues (brain, heart, kidney, muscle, pancreas, tumor, spleen, lung, liver, tail, and muscle) were weighed and then frozen at −80° C. until sub sampling for analysis. Following partial thawing, whole tissues were digested with a mixture of concentrate HNO$_3$ and HCl acids (2:1) at 85° C. for overnight and the aliquots (diluted in water) were used for the analysis by AAS. The results of biodistribution studies for the intravenous route of administration of AuNPs, as estimated by AAS showed minimum uptake of AuNPs in nontarget organs. Limited binding with blood-plasma proteins also signifies the high in vivo stability, presumably due to the effective coating of the phytochemicals around the AuNPs. The significant accumulation of Cin-AuNPs in lung is almost identical from 4 h to 24 h. In addition, there is also a gradual accumulation of gold nanoparticles in liver for up to 24 h. This accumulation in the liver may be due to the uptake of nanoparticles by the macrophages (Kupffer cells) present in the liver. However, no toxic side effects were noted even at the 24-h post-injection period. Indeed, the excellent tolerance of high concentrations of injectable gold agents, for example, myochrysine as demonstrated in humans, provides significant future prospects in the application of AuNPs to tumor imaging and therapy.

The portions of IV dose retained in liver at 4 h and 24 h sacrifice time are ~9% and ~14%, while in lungs, ~17% and ~16% respectively for mice treated with Cin-AuNPs at doses of 200 μL solution (3.75 mg/mL). The amount of nanoparticulate gold found in the kidneys represented <1% of the total dose, thus indicating clearance of AuNPs at a slow pace. This shows that the gold nanoparticles of the invention are bound tightly within the cinnamon phytochemicals and that the carbohydrate part of the cinnamon apparently serves as a vehicle to deliver AuNPs to lungs and liver with minimal distribution of AuNPs to other nontarget organs. This selective delivery of Cin-AuNPs to lungs and liver may provides an unprecedented approach for the molecular imaging of target organs via X-ray contrast CT imaging.

CT imaging was carried out using phantoms prepared from Cin-AuNPs constructs as tissue mimics. Phantom images obtained at 80 and 140 kVp showed higher mean density of gold compared to the background results in a contrast differential ΔHU (HU=Hounsfield units). HU values were measured for increasing amounts of Cin-AuNPs and results showed a linear relationship observed between Cin-AuNPs concentration and ΔHU. Quantitative analysis of CT values for each concentration reveals that the cinnamon phytochemicals coated AuNPs has consistent attenuation coefficients with increasing concentrations. This result clearly suggests that Cin-AuNPs may have a high potential for use in in vivo CT imaging.

Additional EGCg Experimental Results—Synthesis and Characterization

Synthesis an Characterization of EGCg-AuNP:

A non-radioactive surrogate EGCg-AuNP was synthesized by simple mixing of sodium tetrachloroaurate (NaAuCl$_4$) with (−)(EGCg) in deionized water (Scheme 1). This reaction utilizes the strong chemical reduction properties of EGCg to convert gold salt into gold nanoparticles without the intervention of any toxic chemical. The redox potential of AuCl$_4^-$/Au (+0.99V vs. Standard Hydrogen Electrode (SHE)) is significantly positive as compared to the redox potential of EGCg (+0.42V vs. SHE), resulting in a thermodynamically feasible redox couple of AuCl$_4^-$/EGCg leading to the reduction of AuCl$_4^-$ by EGCg to form gold nanoparticles.

Synthesis and Characterization of Radioactive $^{198}$AuNP-EGCg Therapeutic Agent:

The radioactive $^{198}$AuNP-EGCg was synthesized adopting the same protocol optimized for the non-radioactive surrogate, except that the radioactive tetrachloroauric acid (H$^{198}$AuCl$_4$) was used in carrier NaAuCl$_4$ solution or HAuCl$_4$ and the solution was brought to pH 7 and made isotonic using NaOH and Delbecco's phosphate buffered saline. The UV-Vis spectrum of $^{198}$AuNP-EGCg correlated well with the spectroscopic features observed for the non-radioactive EGCg-AuNP surrogate (at: ~535 nm), indicating similarity of nanoparticulate species at the tracer and macroscopic levels. Radio-TLC confirmed the formation of $^{198}$AuNP-EGCg in ≥99% yields, proving the extraordinary reduction capabilities of EGCg even at tracer levels.

Figure 7:
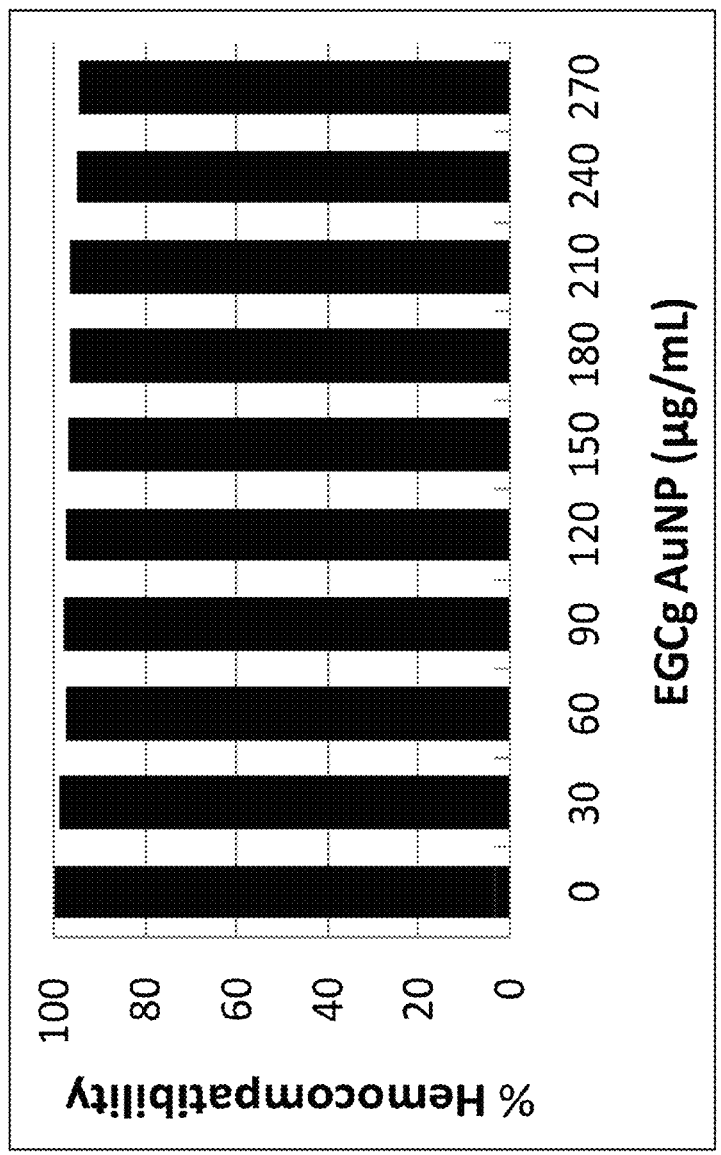
FIG. 7 shows dose dependent hemocompatibility of EGCg-AuNP in human blood.

Hemocompatibility Assessment of EGCg-AuNP:

Non toxic and favorable biocompatibility characteristics of nanomaterials are important considerations in the context of their utility for biomedical applications. EGCg is a catechin abundantly found in green tea and forms a biologically favorable and stable matrix around gold nanoparticles. It is therefore expected that EGCg-AuNP conjugates are biocompatible. FIG. 7 shows dose dependent hemocompatibility of EGCg-AuNP in human blood. The hemocompatibility assay involved direct exposure of EGCg-AuNP to freshly drawn whole human blood for 2 h at 25° C. The results obtained from the hemocompatibility studies confirmed that ≥92% of the RBCs, upon exposure to various concentrations of EGCg-AuNP remained intact, indicating the suitability of the EGCg-AuNPs for various molecular imaging and therapy applications.

Laminin 67 Receptor Mediated Cellular Internalization of EGCg-AuNP:

Of profound significance in conjugating EGCg over AuNPs has been to render targeting capabilities of EGCg-AuNP toward the laminin receptors (Lam 67R), which are over expressed on human prostate cancer cells. In order to prove the affinity of the EGCg-AuNP nanoconstruct toward Lam 67R receptors, qualitative and quantitative prostate cancer receptor binding assays were performed. Laminin 67R is a 67 kDa cell surface protein and its expression has been correlated with aggressiveness and metastatic behavior of a variety of cancers including prostate, breast and colon. Additionally, it has been shown that suppression of the expression of the precursor of Lam 67R (37LBP) using siRNA techniques leads to inhibition of lung cancer cell proliferation in vitro and tumor formation in vivo, clearly indicating the role of Lam 67R in tumorigenicity. Studies by Tachibana et al, have shown that EGCg binds to Lam 67R in prostate cancer cells in a concentration dependent, manner. It is therefore reasonable to hypothesize that EGCg-AuNP internalization in prostate cancer cells (PC-3) through endocytosis will be mediated through Lam 67R receptor expression. In order to investigate this possibilty, the level of Lam 67R expression on PC-3 cells through quantitative RT-PCR and confocal microscopy was monitored using $MLuC_5$ antibody as a probe. The TEM images showed internalization of intact EGCg-AuNP inside PC-3 cells. A detailed analysis of Lam 67R expression in PC-3 cells revealed that a majority of cells expressed Lam 67R transcripts at mRNA levels and are also immunoreactive to $MLuC_5$ antibody, thereby confirming the expression of Lam 67R at transcriptional as well as at post translational levels. After confirming this expression, the PC-3 cells were exposed to various concentrations of EGCg-AuNP. These experiments revealed that a significant amount of EGCg-AuNPs were internalized in PC-3 cells and localized in vacuoles as well as in the cytoplasm without disturbing the nucleus. The dark field microscopic image depicts the visual observation of PC-3 cells following EGCg-AuNP treatment. The internalized nanoparticles are found intact with clear boundaries, confirming high in vitro and in vivo stability of EGCg-AuNPs. The highly efficient cellular uptake of EGCg-AuNPs demonstrates the Lam67R receptor affinity and validates the hypothesis on the creation of prostate tumor specific gold nanoparticles via surface functionalization with EGCg that results in a beneficial and specific affinity uptake.

In order to gain further insights on the receptor specific binding affinity, receptor blocking studies were performed with laminin, the natural ligand for the receptor or Lam 67R specific $MLuC_5$ antibody. Lam 67R receptors were blocked by pretreatment of PC-3 cells with laminin followed by a 90 min incubation with EGCg-AuNPs. The color of the PC-3 cellular pellets turned dark red, when they were not pretreated with laminin, indicating a maximum level of EGCg-AuNP internalization. A decrease in the intensity of the red color in PC-3 cellular pellets pretreated with laminin, indicates significantly reduced endocytosis. Additional proof that the internalization of EGCg-AuNPs within PC-3 cells is mediated by Lam 67R expression came from receptor saturation experiments using Lam 67R specific $MLuC_5$ antibody. In this experiment, Lam 67 receptors were saturated by pre incubating PC-3 cells with $MLuC_5$ antibody (4 µg/mL). Subsequently, these cells were incubated with a large excess of EGCg-AuNP. Saturation of Lam 67R with $MLuC_5$ antibody resulted in a significantly reduced internalization of EGCg within PC-3 cells with consequent reduction, in the intensity of the color of the pellets. The results from the experiments infer that blocking Lam 67R on PC-3 cells either through the laminin or $MLuC_5$ antibody results in saturation of receptors with a concomitant decrease in the internalization of EGCg-AuNP. In order to estimate gold content within PC-3 cells, pre and post treatment with laminin or $MLuC_5$ antibody, quantitative estimation of gold concentrations within samples of PC-3 cells was determined using neutron activation analysis (NAA). NAA measurements estimate the amount of gold in a cell pellet sample and provide the most accurate quantification of the total amount of gold internalized within the cells, allowing direct measurement of cellular uptake of AuNPs. NAA analysis clearly showed a marked decrease in the amount of gold content in PC-3 cells which were pretreated with laminin or $MLuC_5$ antibody as compared with control cells. Blocking of Lam 67R by presaturation either with Lam-67R or $MLuC_5$ antibody on PC-3 cells resulted in significant reduction of gold concentration (~60% and ~85% respectively relative to control cells) in cellular pellets. Therefore, the detailed, studies on the qualitative and quantitative estimation of gold content in PC-3 cell samples have established that the uptake of EGCg-AuNPs within PC-3 cells is mediated through Lam 67R and present opportunities for the selective uptake of therapeutic gold nanoparticles within prostate tumors. Excellent retention of therapeutic payloads of $^{198}$AuNP-EGCg within prostate tumors in mice were attributed to the high affinity of the EGCg functionalized gold nanoparticles toward Laminin receptors. These encouraging data led us to perform detailed therapeutic efficacy studies of $^{198}$AuNP-EGCg and the details are described below.

Figure 8:
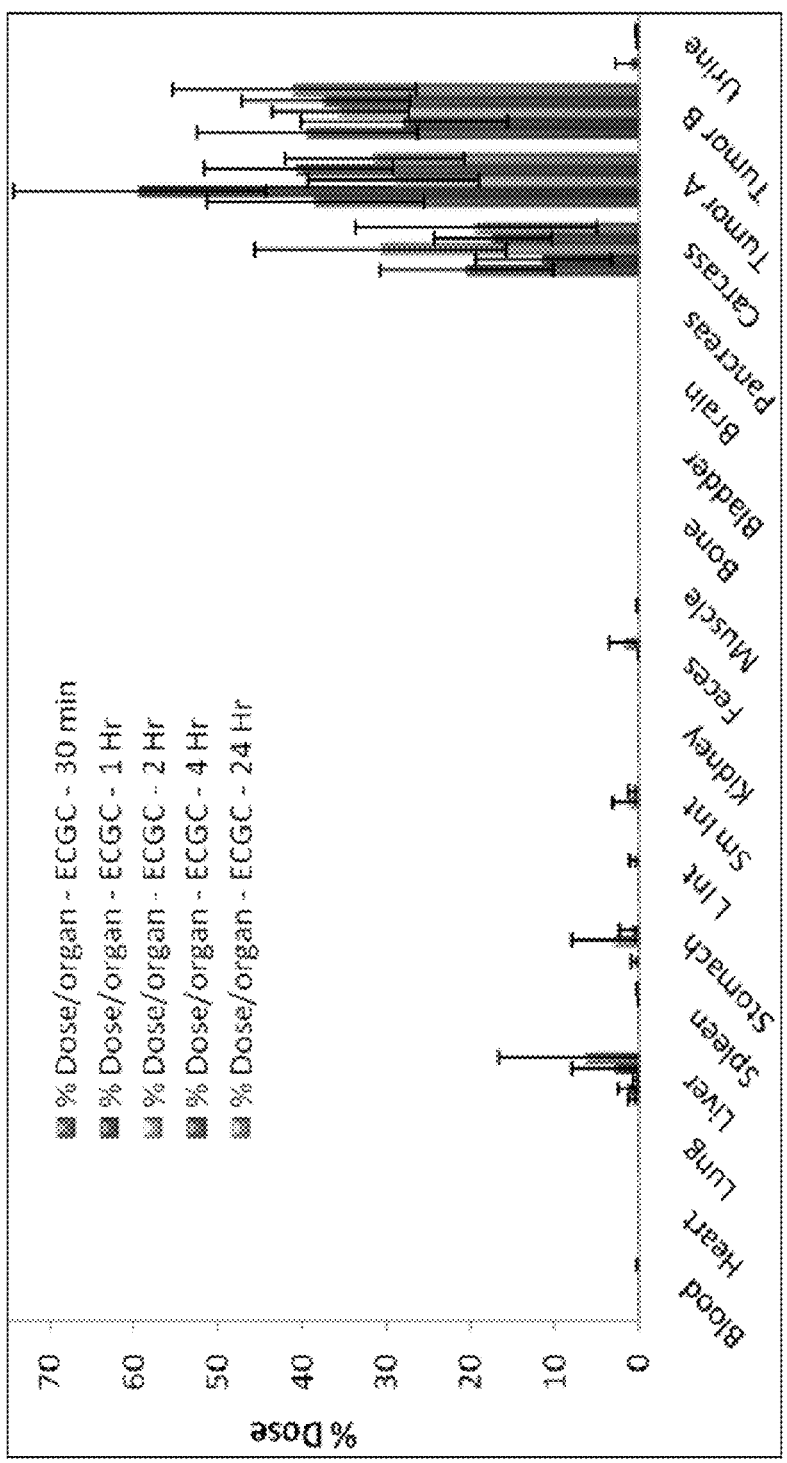
FIG. 8 plots retention of radioactivity in tumors following intra-tumoral injection of $^{198}$AuNP-EGCg in mice (n=5, means±SD)

Pharmacokinetics and Tumor Retention of $^{198}$AuNP-EGCg:

Pharmacokinetic properties of $^{198}$AuNP-EGCg has been investigated in detail as they relate to retention of therapeutic payloads within prostate tumors. The tumor selectivity and retention of Au-198 beta emitting radioactivity are profoundly important in achieving maximum therapeutic efficacy with minimal side effects, in order to achieve maximum therapeutic efficacy, several factors including the size and stability of nanoparticles in the tumor microenvironment, ability of nanoparticles to interact with cells and efficient cellular internalization through active targeting, must all operate in synergy. The present studies have confirmed that over 72% of the injected dose of $^{198}$AuNP-EGCg is retained within prostate tumors up to 24 h. FIG. 8 plots retention of radioactivity in tumors following intra-tumoral injection of $^{198}$AuNP-EGCg in mice (n=5, means±SD).

Figure 9:
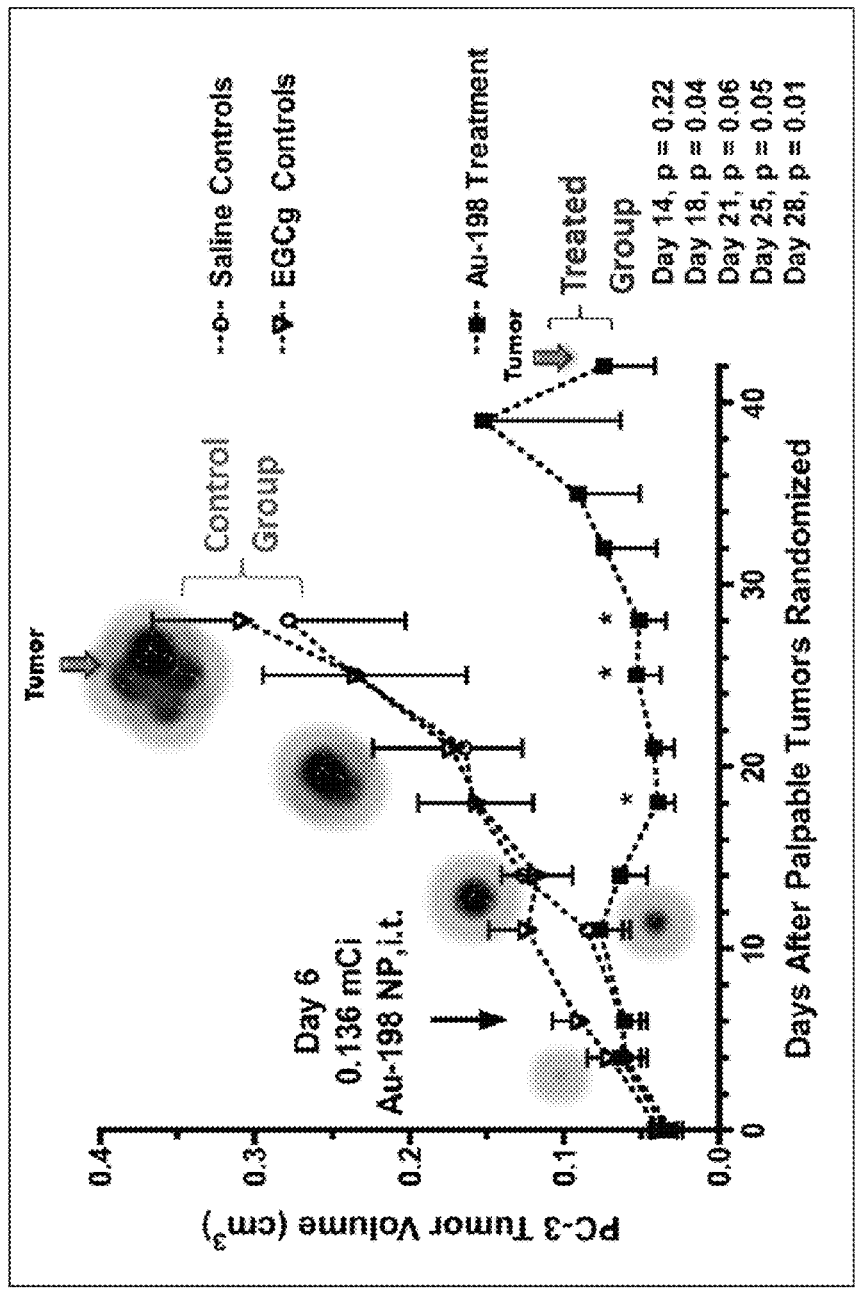
FIG. 9 illustrates therapeutic efficacy of EGCg-AuNPs after a single-dose intra-tumoral administration of $^{198}$AuNP-EGCg in human prostate cancer-bearing SCID mice (means±SEM)

Therapeutic Efficacy Studies of $^{198}$AuNP-EGCg:

A unilateral flank model of prostate cancer derived from human PC-3 cells in SCID mice was utilized. The results from the single-dose radiotherapy study of $^{198}$AuNP-EGCg in human prostate cancer bearing SCID mice are shown in FIG. 9. Within one week after administration of $^{198}$AuNP-EGCg (Day 14), tumor growth in the treated animals appeared to be slowing with respect to controls. By two weeks after $^{198}$AuNP-EGCg administration (Day 18), tumor volumes were four-fold lower (p=0.04) for treated animals as compared to the control group. This significant therapeutic effect was maintained throughout the five week study. By three weeks after $^{198}$AuNP-EGCg administration (Day 28), tumor volumes for the control animals were five-fold greater with respect to those for the radiotherapy group (p=0.01; 0.28±0.08 vs. 0.05±0.02 $cm^3$, means±sem). No significant differences were noted between the DPBS controls and animals treated with EGCg alone in DPBS solutions demonstrating that EGCg in itself did not have any therapeutic effect at this dosage level. After evaluation on Day 21, one animal from each of the EGCg and the DPBS control groups was terminated because of excessive weight loss (>20%). Two additional animals from the EGCg group were terminated due to weight loss on Day 25, and one animal from the $^{198}$AuNP-EGCg group was terminated because of weight loss on Day 39. Studies of the EGCg (n=4) and DPBS control (n=6) groups were concluded on Day 28 due to increasing tumor burdens.

The end-of-study biodistribution on Day 42 showed that 37.4±8.1% ID of $^{198}$AuNP-EGCg (mean±sem; n=5) remained in the residual tumor, while 17.8.±6.1% ID was noted for carcass and 2.5.±1.7% ID was observed in the liver. Retention in other tissues was negligible, with radioactivity near background levels for blood, heart, lung, spleen, intestines, stomach, bone, brain and skeletal muscle.

Blood parameters within the tumor-bearing EGCg and $^{198}$AuNP-EGCg treatment groups, as well as the DPBS controls, showed no significant differences between groups (ANOVA) from each other, or with baseline levels from a fourth group of SCID mice that had not been experimentally manipulated. Comparisons included mean counts for white cells, red cells and lymphocytes, as well as hemoglobin and total protein concentrations. Together, the overall health status and blood measures of the $^{198}$AuNP-EGCg treated animals indicate that the radiotherapy was not only highly effective, but was well tolerated.

Localized Therapy May Achieve Deceleration of Metastases:

The propensity with which EGCg-AuNPs internalize within PC-3 cells is evidenced by the high density of nanoparticles within prostate tumor cells was revealed in TEM images. These results fully corroborate the receptor mediated internalization studies as discussed above. It is important to recognize that the identity of nanoparticles within PC-3 cells is maintained as there are no aggregated domains of gold nanoparticles within the PC-3 cells. As discussed in the therapeutic efficacy studies, intratumoral delivery of $^{198}$AuNP-EGCg nanoparticles within prostate tumors in mice resulted in effective control of tumor growth. Therefore, the highly efficient entry of EGCg-AuNPs across prostate tumor cell membranes has the potential to effectively destroy tumor cells within localized areas. This will prevent cell propagation and recruitment of tumor cells (and stem tumor cells) into bone marrow—a pathway to decelerate and stop metastases of prostate and other solid tumors.

Materials and Methods for the Additional Experiments

Synthesis and Characterization of $^{198}$AuNP-EGCg and its Non-Radioactive Surrogate EGCg-AuNP:

$^{198}$AuNP-EGCgs were synthesized by simple mixing of aqueous solutions of EGCg (Sigma, St. Louis) and radioactive tetrachloroauric acid (H$^{198}$AuCl$_4$) in 0.1M NaAuCl$_4$ carrier solution and the solution was brought to pH 7 and isotonic using NaOH and Delbecco's phosphate buffered saline. University of Missouri Research Reactor (MURR) irradiation facilities were used for the production of $^{198}$Au. Briefly, to a 20 mL vial, 2.2 mg of Epigallocatechin gallate was added in 6 mL of doubly ionized water (DI). The reaction mixture was stirred continuously at 25° C. for 5 min. To the stirring mixture was added 100 µL of H$^{198}$AuCl$_4$ (0.41-1.3 mCi, 2 µL) in 0.1M NaAuCl$_4$ carrier solution. The color of the mixture turned purple-red from pale yellow within 5 min indicating the formation of gold nanoparticles. This reaction mixture was stirred for an additional 15 min at 25C. The gold nanoparticles thus obtained were characterized by UV-Vis absorption spectroscopy.

Plasmon resonance band at ~535 nm indicated the formation of gold nanoparticles. Non-radioactive surrogate EGCg-AuNP was synthesized from non radioactive gold precursor using similar protocols for synthesizing radioactive nanoparticles and used as such for establishing the stability and biocompatibility properties of the conjugates prior to in vivo application of the $^{198}$AuNP-EGCg for therapy. Photophysical properties and size of EGCg-AuNPs were measured using transmission electron microscopy, dynamic light scattering and zeta potential measurement. The stability studies of EGCg-AuNP in biologically relevant solutions (10% NaCl, 0.5% cysteine, 0.2M histidine, 0.5% HSA and different pH buffers (7, 9)

Characterization and In Vitro Stability of EGCg-AuNPs.

The surface plasmon resonance wavelength, $\lambda_{max}$, and plasmon band width, $\Delta\lambda$, of EGCg-AuNPs are ~535 nm and 65 nm respectively, indicating the formation of EGCg-AuNP. The core size of the EGCg-AuNP is 40-55 nm, as determined from TEM images, while the hydrodynamic radius revealed that 95% of EGCg-AuNP conjugates have an average diameter of 120-1.30 mm. This implies that the EGCg coating over AuNP occupies ~85 nm. The zeta potential, is an indication of repulsive forces that are present in aqueous solution and can be used to predict the long-term in vitro/in vivo stability of nanoparticulate dispersions. The high zeta potential of −37.7 mV as observed for EGCg-AuNP is a clear indication of its high stability against aggregation.

The stability of EGCg-AuNP was evaluated in various biological fluids to establish its intended utility under in vivo conditions. Solutions of EGCg-AuNP were challenged with 10% NaCl, 0.2M histidine, 0.5% human serum albumin (HSA), 0.5% Bovine Serum Albumin (BSA) and at various pH values (7, 9) and the stability was monitored through changes in surface plasmon resonance ($\lambda_{max}$) and plasmon band width ($\Delta\lambda$). The $\lambda_{max}$ and $\Delta\lambda$ in all of the above media shilied by only ~10 nm indicating excellent in vitro stability. Further in vitro stability of EGCg-AuNPs was assessed by incubating the nanoparticles in cell culture media. No detectable aggregation/decomposition was noted in these experiments. The non-radioactive EGCg-AuNPs were determined to be stable at room temperature without any noticeable aggregation over a period of 12 months when stored at 25° C. in closed vials. The in vitro studies have validated stability of EGCg-AuNPs in biological fluids at physiological pH suggesting that EGCg coating provides a robust shielding around AuNPs, thus rendering in vitro stability. It is significant to note that no additional capping agent was used during the synthesis of EGCg-AuNPs indicating that the FDA approved phytochemical EGCg serves as both a reducing and capping agent to produce in vitro and in vivo stable AuNPs.

Synthesis of $^{198}$AuNP-EGCg.

Gold leaf (0.76 mg) was irradiated for 3.5 h. The calculated activity of $^{198}$Au was 20.5 mCi according to the Capintec® CRC-12. The $^{198}$Au foil was placed in a Liquid Scintillation Counting (LSC) vial and dissolved in 800 µL of aqua regia. The solution was heated to reduce the volume to approximately 200 µL. Then 600 µL of 0.05M HCl was added and heating continued until most of the acid had evaporated. The solution was removed from the hot plate and allowed to cool followed by the addition of 200 µL of 0.05M HCl. A 0.17 mg/mL solution of EGCg was prepared in Milli-Q water and stirred continuously at 25° C. for 3 min. To the stirring mixture was added 2 µL of H$^{198}$AuCl$_4$ (0.41-1.3 mCi,) and 98 µL of 0.1M NaAuCl$_4$ carrier solution. The color of the mixture turned purple-red from pale yellow within 5 min indicating the formation of gold nanoparticles. The reaction mixture was stirred for an additional 15 min at 25° C. The UV-Vis spectrometer was used to characterize $^{198}$AuNP-EGCg. The homogeneous distribution of nanoparticles in $^{198}$AuNP-EGCg was ascertained by observing the Plasmon absorption band and the band width. The formation of AuNP was monitored through a color change from yellow to purple red. Solutions were evaluated by spectrophotometry on an Ocean Optics USB2000 to confirm the formation of $^{198}$AuNP-EGCg. The change in color from pale yellow to purple red is diagnostic of a plasmon-plasmon transition present in gold nanoparticles. The plasmon absorption band at 535 nm with the width of 90 nm was considered as homogeneous distribution.

In order to ascertain the percent conversion of $^{198}$AuCl$_4^-$ to nanoparticles, standard thin layer chromatography technique was used to differentiate the unreacted $^{198}$AuCl$_4^-$ from the $^{198}$AuNPs. A radiochemical purity and percent labeling was tested by TLC on Whatman cellulose paper. Briefly 3 μL of the solution was spotted onto Whatman cellulose plates and developed in methanol (2 mL) with 1 drop of concentrated HCl (~10 M). The paper strip was scanned on a BioScan to determine the percent radiolabeling yield. The $^{198}$AuNP-EGCg functionalized nanoparticles remains at the origin $R_f=0$, and free $^{198}$AuCl$_4$-migrates with an $R_f$ of 0.9. The radiolabeling yield was >99%.

Hemocompatibility Studies.

Hemolytic studies were used to assess the biocompatibility of nanoparticles by direct exposure to freshly drawn human blood from healthy volunteers. The nanoparticles were tested for hemolysis and a quantitative colorimetric assay for hemoglobin release was performed. Briefly, fresh blood from two human volunteers was drawn, collected in CPI) (Citrate Phosphate Dextrose) solution and due care was taken for thorough mixing to achieve homogeneity. The cells were thoroughly washed with veronal buffered saline (VBS) containing 5 mM barbital and 145 mM NaCl (pH 7.4). After 3-4 washes, when the supernatant was clear, the packed RBCs fraction was adjusted by diluting in such a way that RBC lysate in water gave an optical density (OD) of 1 at 405 nm. The adjusted RBC solution was kept on ice and was used in duplicates by mixing 10 μL of RBC suspension with increasing concentrations of EGCg-AuNP and the final volume of each tube was adjusted to 100 μL by addition of VBS. The tubes were incubated at 37° C. for 2 h with occasional mixing by gentle tapping. RBC lyses in water was considered 100% while in VBS was considered 0%. After incubation, 200 μL of VBS buffer was added to each tube and centrifuged at 3000 rpm for 2 min in a refrigerated centrifuge. A 100 μL aliquot of supernatant from each tube was added to each of 96 well ELISA plate in duplicates and the extent of RBC lyses determined at 405 nm in Spectra Max plate reader (Molecular Device, USA).

Cellular Internalization of EGCg-AuNP:

Cellular internalization of EGCg-AuNP was studied by three independent techniques. While qualitative internalization was assessed by two independent microscopic methods, the quantitative cellular uptake of EGCg-AuNP was estimated by neutron activation analysis (NAA). PC-3 prostate cancer cells in their log phase of growth were seeded in 60 mm plates at a cell density of $2\times10^5$ cells/plate. These cells were incubated until the plates achieved ~70% confluence. To block the receptor mediated internalization of EGCg-AuNP through Laminin 67R, the cells were pretreated with either 1 μg/mL laminin (sigma) or 4 μg/mL, of anti-Lam 67R antibody for 30 min and then exposed to 30 μg/mL EGCg-AuNP for 90 min. In all of our experiments, untreated cells (cells that were not treated with EGCg-AuNP) were used as controls. Post incubation, cells were washed thoroughly, pelleted, fixed in alcohol, photographed and subjected to NAA analysis (details in supporting information). In the second set of experiments, the cells, after treatment with EGCg-AuNP for 4 h followed by extensive washings, were dislodged, pelleted, fixed and processed for electron microscopy.

For dark field microscopy studies, cells were grown on cover slips until ~70% confluence was achieved. The cells were pretreated following similar procedures as described in the section on NAA analysis: with 4 μg/mL of anti-Lam 67R antibody for 30 min and then exposed to 30 μg/mL EGCg-AuNP for 4 h. Untreated cells were used as controls and the cells that were not pretreated with antibody but treated with EGCg-AuNP were used for comparison.

Tumor Retention Capabilities of $^{198}$AuNP-EGCg.

To monitor the tumor retention capabilities, Intratumoral (IT) injections of $^{198}$AuNP-EGCg nanoparticles were performed in severely compromised immunodeficient (SCID) mice bearing bilateral flank tumor xenografts of human PC-3 prostate cancer. Each tumor was injected with 20 μl (3.5 μCi) of $^{198}$AuNP-EGCg in Dulbecco's PBS (DPBS). Analysis of $^{198}$Au radioactivity revealed that 72.4±5.9% ID (mean±sem, n=5) of $^{198}$AuNP-EGCg nanoparticles was retained in prostate tumors at 24 h. and was nearly constant from 30 min (77.8±5.5) to 24 h. The $^{198}$AuNP-EGCg nanoparticles exhibited slow clearance (leakage) into the blood with only 0.06% ID/g at 24 h. Lungs and pancreas exhibited low uptake at 24 h with only 0.33% ID/g and 0.22% ID/g, respectively. The uptake in the stomach peaked at 5% ID/g at 2 h and decreased to 0.03% ID/g at 24 h. The highest uptake in the small intestines was observed at 2 h with 0.91% ID/g that reduced to 0.01% ID/g at 24 h. The kidneys and spleen showed slow uptake over time with 0.12% ID/g and 1.56% ID/g at 24 h. The liver had 0.51% ID/g after 30 min and increased to 6.13% ID/g after 24 h. The gastrointestinal uptake mentioned above contributed to the feces having 1.71% ID after 24 h. These pharmacokinetic features confirmed excellent retention of therapeutic payloads of $^{198}$AuNP-EGCg nanoparticles within prostate tumors with only minor leakage to non target organs.

Blood Parameters for Therapeutic Efficacy.

Blood parameters were compared between the $^{198}$AuNP-EGCg treatment (n=6), EGCg control (n=6) and saline control (n=7) groups with baseline levels obtained from a fourth group (n=7) of normal SCID mice that received no manipulations. One blood sample from the non-radioactive EGCg group clotted, and was excluded from analysis. Blood from all animals euthanized in mid-study were analyzed immediately, and those values were included with data from animals euthanized at the end-of-study. Analysis of variance showed no significant differences (p>0.05) between any of the groups for any blood parameters.

Biodistribution and Therapeutic Efficacy Studies of $^{198}$AuNP-EGCg:

All in vivo studies were conducted in compliance with the Guide for the Care and Use of Laboratory Animals under approvals from the Institutional. Animal Care and Use Committees of the Harry S. Truman Memorial Veterans' Hospital and the University of Missouri, Female ICRSC-M SCID mice (4-5 weeks of age; Taconic Farms, Hudson, N.Y.) were group housed on a 12 h light-dark cycle in a pathogen-free barrier facility having controlled temperature and humidity. Animals had access to sterilized standard chow and water ad libitum, and were acclimated for 7-10 days prior to manipulations. The PC-3 human prostate cancer cell line was obtained from the American Type Culture Collection (ATCC; Manassas, Va.), Biodistribution Studies:

Mice received bilateral subcutaneous hind flank inoculations of $10\times10^6$ PC-3 cells (passage 20) suspended in 0.1 mL of sterile Dulbecco's phosphate buffered saline (DPBS) and Matrigel® (2:1, v:v) under inhalational anesthesia (isoflurane/oxygen). Solid tumors were allowed to develop for four weeks, and animals were randomized into five groups (n=5). Animals in each group received intratumoral (i.t.) injections of $^{198}$AuNP-EGCg (3.5 μCi) in DPBS (20 μL) while under brief inhalational anesthesia. Groups were euthanized by cervical dislocation at intervals of 30 min, 1, 2, 4 and 24 h. Blood samples were obtained by cardiac puncture. Urine and Feces were collected from cage papers representing the entire time interval. Tumors and organs of interest were harvested, weighed and then counted using an automated γ-counter to determine the percent injected dose per gram (% ID/g) and per organ at each time. Mean tumor weights for the five groups ranged from 0.18 to 0.23 g, with no significant differences (p>0.05, ANOVA) between groups.

Therapeutic Efficacy Studies:

A colony of 21 female SCID mice bearing PC-3 tumors from cell passage 21 was established as described above, except a unilateral right flank model was employed, and animals received ear tag identifiers while under inhalational anesthesia. Solid tumors developed over a period of 22 days, and animals were then randomized (denoted Day 0) into a control and two treatment groups (n=7) having no significant differences (ANOVA) in tumor volumes (p=0.69) or body weights (p=0.23) between groups. Tumor volumes were determined by caliper measurements using the formula V=length×width×depth. Group mean tumor volumes ranged from 0.031-0.041 cm$^3$, while group mean body weights ranged from 22.6-24.0 g. Under inhalational anesthesia on Day 6, one treatment group received $^{198}$AuNP-EGCg (136 μCi) in DPBS (30 μL, i.t.) while the second treatment group received the non-radioactive EGCg formulation in PBUS (30 μL, i.t.). The control group received only DPBS (30 μL, i.t.). On the day of treatment, one animal in the $^{198}$AuNP-EGCg group displayed a tumor volume that was two standard deviations above the group mean, and near the critical score for an outlier using the Grubbs' test. This animal was removed from further analysis, leaving an $^{198}$AuNP-EGCg group (n=6) that showed no significant difference (p=0.69; ANOVA) in tumor volumes with the non-radioactive EGCg and DPBS control groups (n=7) on Day 6.

Figures 10A, 10B:
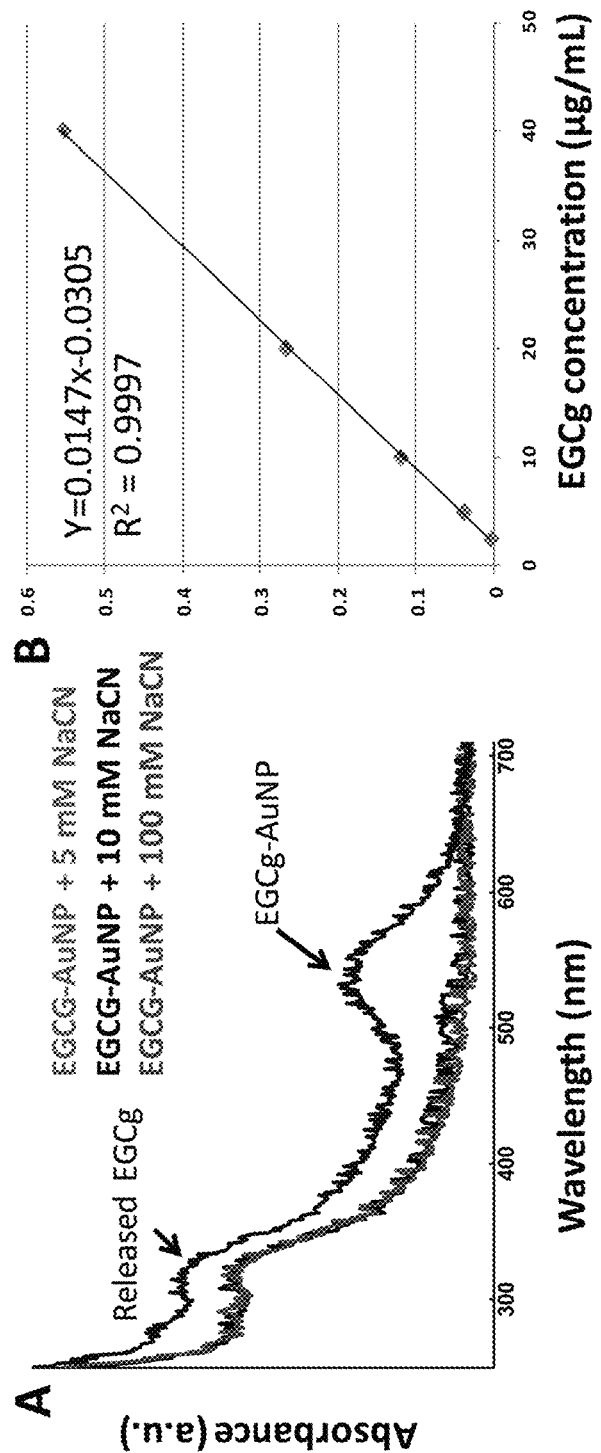
FIGS. 10A and 10B illustrate estimation of amount of EGCg conjugated to EGCg-AuNPs.

Overall health evaluations, including measurements of tumor volumes and body weights, were conducted twice each week. Euthanasia was by cervical dislocation, and blood samples were collected (K$_3$-EDTA; Vacuette Mini-Collect®) by cardiac puncture for all animals. End of study for the $^{198}$AuNP-EGCg treatment group was on Day 42. These animals (n=5) were euthanized by cervical dislocation, and blood samples were collected by cardiac puncture and treated as described above. Samples of tumor, carcass and organs of interest were harvested, weighed and counted for radioactivity in comparison to a sample of the injected dose using an automated γ-counter. Complete blood counts (CBC) for the fresh bloods were determined by the University of Missouri Research Animal Diagnostic Laboratory (RADIL) using an Abbott Cell-Dyn® 3500 analyzer. These values were compared (ANOVA) to those from fresh bloods obtained from a separate group of female ICRSC-M SCID mice (n=7) that received no experimental manipulations, and were maintained through the end of the study, Unique Characterization Method for EGCg-AuNP The effective number of EGCg coated on the surface of gold nanoparticles is important to understand the overall stability, size, charge, and therapeutic efficacy. A new method was developed to quantitatively estimate the amount of EGCg on the surface of gold nanoparticles: sodium cyanide digestion experiments (NaCN). Testing used EGCg-AuNPs samples that were previously centrifuged and after repeated washing with DI water to ensure complete removal of unreacted and unbound EGCg. 1 mL of EGCg-AuNP was centrifuged at 19000 rpm (RC5 plus refrigerated centrifuge with ss-34 rotor) at 10° C. for 30 min. The supernatant was discarded and the pellet was washed twice by replenishing with 1 mL of DI water. Finally, the pellet was suspended in 1 ml DI water and sonicated to produce homogeneous nanoparticle suspension. A 50 μL of this solution was digested with 0.01M NaCN solution (2 mL final volume) for 60 min followed by UV-Visible spectral analysis. Spectrophotometric analysis pure EGCg samples in 0.01M NaCN solutions gave a $\lambda_{max}$ at 330 nm. The corresponding $\lambda_{max}$ for EGCg-AuNPs is at 535 nm. EGCg-AuNPs were titrated with various concentrations of NaCN in order to digest EGCg bound to the nanoparticles and thereby calculate the amount of EGCg bound to gold nanoparticles. Through spectrophotometric analysis, we have therefore, monitored the disappearance of the peak at 535 nm (due to EGCg-AuNPs) and followed increases in the extinction coefficient of the peak at 330 nm (due to released EGCg). FIGS. 10A and 10B demonstrates that the digestion EGCG-AuNPs with 0.01M NaCN releases the EGCG hound to gold nanoparticles as the peak at 535 nm continued to decrease in intensity while the intensity of the peak at 330 nm increased until all the bound EGCg was completely removed from the surface of gold nanoparticles. The plotting of various concentrations of solution of EGCg in 0.01M NaCN verses optical density provides quantitative estimation of bound EGCg on gold nanoparticles. From these studies, one can infer that over 90% of the free EGCg used in the preparation of AuNPs remains bound to gold nanoparticles to produce EGCg-AuNPs. It may be noted that the above calculations have an excellent accuracy because spectrophotometric analysis using known concentration of EGCg through extinction coefficient measurements gave an error of 1%.

Multi-Layered Nanoparticles

Multi-layer coatings are formed via a modified process that uses a pre-cooled aqueous solutions of gold salts and EGCg solution. Compared to room-temperature experiments that tend to produce a single layer of EGCg on gold nanoparticles (typically ~10 nm-20 nm coating on 40 nm gold nanoparticles), the experiments with pre-cooled nanoparticles and EGCg solutions.

Experiments were conducted to form 3 batches of multi-layer EGCg-AuNP (RS) and control room temperature (RT) single layer EGCg. In the RS experiments, 2.2 mg of EGCG was equilibrated at 4° C. for 15 min added to 6 mL of cold water (4° C.) and allowed to dissolve to obtain clear solution. Added to this clear solution was 100 ul of 0.1M NaAuCl$_4$, solution pre cooled at 4° C. The solution incubated at 4° C. for 60 min. Upon addition of NaAuCl$_4$, solution turns ruby red in 5 min. After incubation, the following physic chemical properties were monitored.

Lot nos. were assigned as in the following table:

EGCG-AuNP061311-01RS
EGCG-AuNP061311-02RS
EGCG-AuNP061311-03RS
EGCG-AuNP061311-RT-RS

The formed EGCg gold nanoparticles were characterized as follows:

| Lot No. | Sample code | Zeta potential mV | Hydrodynamic radius nm | UV-Vis nm | Calculated conc. mg/mL | NAA |
|---|---|---|---|---|---|---|
| EGCG-AuNP061311-01RS | EGCG-AuNP061311-01RS | −43.2<br>−44.6<br>−44.0 | 60.04<br>60.42<br>61.45 | 535 | 320 PPM | |

-continued

| Lot No. | Sample code | Zeta potential mV | Hydrodynamic radius nm | UV-Vis nm | Calculated conc. mg/mL | NAA |
|---|---|---|---|---|---|---|
| EGCG-AuNP061311-02RS | EGCG-AuNP061311-02RS | −38.7<br>−39.3<br>−38.6 | 53.74<br>53.46<br>53.93 | 535 | 320 ppm | |
| EGCG-AuNP061311-03RS | EGCG-AuNP061311-03RS | −47.0 | 61.72<br>62.2<br>61.16 | 535 | 320 ppm | |
| EGCG-AuNP061311-RT-RS | EGCG-AuNP061311-RT-RS | −44.0<br>−44.9<br>−44.5 | 94.13<br>93.92<br>93.98 | 540 | 320 ppm | |
| EGCG-AuNP061411-RS | EGCG-AuNP061411-RS | −55.6<br>−53.8<br>−55.2 | 37.63<br>37.84<br>37.71 | 540 | 320 ppm | |

Example Therapies

The testing in mice shows that the present EGCg Au$^{198}$NP is an important clinical development indicating the potential for clinical translation of this agent in reducing the size of various other solid tumors prevalent in human and animal populations. Intratumoral delivery of EGCg-Au$^{198}$NPs can circumvent vascular and interstitial transport barriers resulting in targeted delivery of optimal therapeutic payloads with minimal/no toxicity to neighboring tissue. The present combinatorial nanomedicine invention presents realistic potential in the effective treatment of hormone refractory prostate tumors and various other human tumors which manifest resistance in response to cell killing therapies, and therefore will extend survival as the tumors are transformed to be static.

While specific embodiments of the present invention have been shown and described, it should be understood that other modifications, substitutions and alternatives are apparent to one of ordinary skill in the art. Such modifications, substitutions and alternatives can, be made without departing from the spirit and scope of the invention, which should be determined from the appended claims.

Various features of the invention are set forth in the appended claims.

The invention claimed is:

1. An environmentally friendly method for making epigallocatechin Gallate (EGCg) stabilized gold nanoparticles, the method comprising:
   mixing a solution of epigallocatechin Gallate (EGCg) as a reducing agent with an aqueous solution containing gold salts;
   permitting reaction of the gold salts, in the absence of any other reducing agent, to form stabilized, biocompatible gold nanoparticles.

2. The method of claim 1, wherein the solution containing gold salts comprises $AuCl_4$.

3. The method of claim 2, wherein the solution of EGCg comprises deionized water.

4. The method of claim 3, wherein the solution of gold salts comprises carrier $NaAuCl_4$ solution.

5. The method of claim 4, wherein the carrier $NaAuCl_4$ solution is adjusted to a neutral pH and isotonic.

6. The method of claim 1, wherein the solution of gold salts comprises $H^{198}AuCl_4$.

7. The method of claim 6, wherein the solution of EGCg comprises deionized water.

8. The method of claim 7, wherein the solution of gold salts further comprises a carrier $NaAuCl_4$ solution.

9. The method of claim 8, wherein the carrier $NaAuCl_4$ solution is adjusted to a neutral pH and isotonic.

10. The method of claim 1, further comprising a step of heating the aqueous solution during said step of permitting reaction.

11. The method of claim 10, wherein said step of heating comprises microwave heating.

12. The method of claim 1, further comprising a step of adjusting the pH of the aqueous solution after said step of permitting reaction.

13. The method of claim 1, further comprising a step of adding a stabilizing agent to the aqueous solution after said step of permitting reaction.

14. The method of claim 13, wherein said stabilizing agent comprises gum Arabic.

15. The method of claim 1, wherein the gold salts comprises either sodium tetrachloaurate or aurochloric acid.

16. The method of claim 1, wherein the solution containing gold salts and the solution of EGCg are pre-cooled below room-temperature prior to said mixing.

17. The method of claim 16, wherein the solution containing gold salts and the solution of EGCg are pre-cooled to ~4° C. and equilibrated.

* * * * *

UNITED STATES PATENT AND TRADEMARK OFFICE
CERTIFICATE OF CORRECTION

PATENT NO. : 9,358,310 B2  
APPLICATION NO. : 13/668916  
DATED : June 7, 2016  
INVENTOR(S) : Kattesh V. Katti et al.

Page 1 of 1

It is certified that error appears in the above-identified patent and that said Letters Patent is hereby corrected as shown below:

In the Specification

Column 1, Line 19 Please delete "National Cancer Institute" and insert --National Institutes of Health-- therefor.

Signed and Sealed this  
Twenty-fifth Day of January, 2022

Drew Hirshfeld  
*Performing the Functions and Duties of the*  
*Under Secretary of Commerce for Intellectual Property and*  
*Director of the United States Patent and Trademark Office*